United States Patent
Xuan et al.

(10) Patent No.: US 11,193,153 B2
(45) Date of Patent: Dec. 7, 2021

(54) PROGRAMMABLE NUCLEIC ACID SYNTHESIS CASCADE

(71) Applicant: President and Fellows of Harvard College, Cambridge, MA (US)

(72) Inventors: Feng Xuan, Boston, MA (US); Jocelyn Yoshiko Kishi, Boston, MA (US); Peng Yin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 146 days.

(21) Appl. No.: 16/495,721

(22) PCT Filed: Mar. 19, 2018

(86) PCT No.: PCT/US2018/023096
§ 371 (c)(1),
(2) Date: Sep. 19, 2019

(87) PCT Pub. No.: WO2018/175296
PCT Pub. Date: Sep. 27, 2018

(65) Prior Publication Data
US 2020/0109426 A1 Apr. 9, 2020

Related U.S. Application Data

(60) Provisional application No. 62/473,873, filed on Mar. 20, 2017.

(51) Int. Cl.
*C12P 19/34* (2006.01)
*C12Q 1/6853* (2018.01)

(52) U.S. Cl.
CPC ............ *C12P 19/34* (2013.01); *C12Q 1/6853* (2013.01); *C12Q 2531/119* (2013.01)

(58) Field of Classification Search
CPC ........................ C12Q 1/6853; C12Q 2525/121
See application file for complete search history.

(56) References Cited

U.S. PATENT DOCUMENTS

| 7,094,536 | B2 | 8/2006 | Kurn |
| 7,351,557 | B2 | 4/2008 | Kurn |
| 2005/0227259 | A1 | 10/2005 | Zhang et al. |
| 2006/0035275 | A1 | 2/2006 | Ward et al. |
| 2007/0031885 | A1 | 2/2007 | Marshall et al. |
| 2009/0011956 | A1 | 1/2009 | Yin et al. |
| 2009/0203085 | A1* | 8/2009 | Kurn ..................... C12Q 1/686 |
| | | | 435/91.2 |
| 2012/0009649 | A1 | 1/2012 | Dahl et al. |
| 2012/0022146 | A1 | 1/2012 | Han et al. |
| 2015/0152409 | A1 | 6/2015 | Seitz et al. |

FOREIGN PATENT DOCUMENTS

WO    WO 2016/161380 A1    10/2016

OTHER PUBLICATIONS

Peleg, O. et al., Use of Chimeric DNA-RNA Primers in Quantitative PCR for Detection of Ehrlichia canis and Babesia canis, Appl. Env. Microbiol., vol. 75, pp. 6393-6398 (Year: 2009).*
Seyfang et al., Multiple site-directed mutagenesis of more than 10 sites simultaneously and in a single round. Anal Biochem. Jan. 15, 2004;324(2):285-91.
Singh et al., Microarray-based comparison of three amplification methods for nanogram amounts of total RNA. Am J Physiol Cell Physiol. May 2005;288(5):C1179-89. Epub Dec. 21, 2004.

* cited by examiner

*Primary Examiner* — Teresa E Strzelecka
(74) *Attorney, Agent, or Firm* — Wolf, Greenfield & Sacks, P.C.

(57) ABSTRACT

The present disclosure provides, in some embodiments, methods and compositions for exponential amplification of single- and double-stranded DNA under isothermal conditions.

12 Claims, 12 Drawing Sheets
Specification includes a Sequence Listing.

Fluorescent concatemers

Precise molecular positioning on scaffold

Landscape 'collecting'

Landscape 'crawling'

Time (min)

▷ = unextendable linker
   or unextendable oligonucleotide sequence

● = RNA base or bases

R1:

R2:

R3:

R4:

FAM

R1   R2   R3   R4

PROGRAMMABLE NUCLEIC ACID SYNTHESIS CASCADE

RELATED APPLICATION

This application is a national stage filing under 35 U.S.C § 371 of international application number PCT/US2018/023096, filed Mar. 19, 2018, which claims the benefit under 35 U.S.C. § 119(e) of U.S. provisional application No. 62/473,873, filed Mar. 20, 2017, each of which is incorporated by reference herein in its entirety.

FEDERALLY SPONSORED RESEARCH

This invention was made with government support under N00014-16-1-2410 awarded by the Office of Naval Research. The government has certain rights in the invention.

BACKGROUND

Cells use RNA primers to initiate replication of their genome by a DNA polymerase before cleaving the RNA primers to produce the complete DNA product.

SUMMARY

The present disclosure provides compositions, methods and kits that tie together DNA polymerization and RNA digestion to dynamically, isothermally and autonomously produce single-stranded and double-stranded DNA transcripts in a programmable and efficient manner. Chimeric templates that include a mixture of DNA and RNA bases, for example, are used to append sequences to the 3' end of 'growing' primer strands. Examples of basic reactions implemented using the compositions and methods of the present disclosure are shown in FIGS. 1A and 1B. In both examples, a template strand 'b* a*' patterns the appendage by DNA polymerase of domain 'b' onto the 3' end of a primer comprising domain 'a'. The template strands typically include a modification, such as an inverted dT base or a series of 'T' bases, on their 3' end to prevent extension by a DNA polymerase.

Unlike reaction cascades that require nicking site sequences for digestion, the method provided herein is not so limited by these specific sequences. Further, because the complement template strand is digested (rather than the synthesized strand), this technology may be used to synthesize relatively longer polymers (e.g., greater than 1 kb, 5 kb, or 10 kb), enabling a wide range of molecular recording and amplification applications. For example, the synthesis reactions of the present disclosure may be used for isothermal exponential amplification of nucleic acid, for ultraspecific target detection through kinetic proofreading (e.g., of rare nucleic acid targets or other nucleic acid targets present at concentrations as low as 10 nM), and for molecular assembling and recording. Other applications are contemplated herein.

As shown in FIGS. 1A and 1B, a synthesis reactions occur in three main steps. First, primer 'a' binds to complementary sequence 'a*' on a template strand (step 1). Next, a DNA polymerase 'copies' complement 'b' of adjacent domain 'b*' of the template strand onto the 3' end of the primer (step 2). In the example shown in FIG. 1A, domain 'b*' includes intercalated RNA (dots) and DNA (lines) bases. In the example shown in FIG. 1B, both domains 'a*' and 'b*' include intercalated RNA (dots) and DNA (lines) bases.

Lastly, the RNA bases (dots) in the newly created double-stranded nucleic acid are cleaved by an RNase H enzyme (step 3), leaving domain 'b' exposed (FIG. 1A) or leaving both domains 'a' and 'b' exposed (FIG. 1B). These synthesis reactions can be combined together in programmable reaction cascades to produce largely double-stranded nucleic acids (see, e.g., FIG. 1A and FIG. 1C) or single-stranded nucleic acids (see, e.g., FIG. 1B and FIG. 1D), for example.

With conventional amplification methods, such as PCR, the maximum rate of amplification is limited by the time it takes to cycle through different temperatures. The number of copies can only double one time per cycle, each of which typically lasts at least several minutes. The technology of the present disclosure, by contrast, is not limited by thermal cycling parameters, such as annealing temperature and extension time. Rather, the present technology can be performed 'automatically' at a range of constant operating temperature conditions using, for example, two short primer sequences per target sequence and can generate more than two copies of each target per round of amplification. This eliminates the need for expensive thermal cyclers and permits exponential amplification in more permissive environments relative to conventional nucleic acid amplification techniques.

Thus, some aspects of the present disclosure provide methods of producing a nucleic acid comprising: combining in reaction buffer that contains a polymerase (a) a template strand comprising (i) a 5' domain that comprises deoxyribonucleotides interspersed with ribonucleotides, and (ii) a 3' domain, and (b) a primer strand comprising a nucleotide domain that is complementary to the 3' domain of the template strand; incubating the reaction mixture under conditions that result in DNA polymerization to produce a double-stranded nucleic acid; an incubating the double-stranded nucleic acid in reaction buffer that contains ribonuclease H (RNase H) under conditions that result in enzymatic cleavage of the double-stranded nucleic acid.

Also provided herein, in some aspects, are compositions comprising (a) a polymerase, (b) a template strand comprising (i) a 5' domain that comprises deoxyribonucleotides interspersed with ribonucleotides, and (ii) a 3' domain, and (c) a primer strand comprising a nucleotide domain that is complementary to the 3' domain of the template strand. In some embodiments, the compositions further comprise RNaseH. In some embodiments, compositions comprise (a) RNase H, (b) a double-stranded nucleic acid comprising a first strand bound to a second strand, wherein one of the two strands comprises a 5' domain that comprises deoxyribonucleotides interspersed with ribonucleotides.

Other aspects of the present disclosure provide methods of producing a nucleic acid comprising: combining in reaction buffer that contains a strand-displacing polymerase (a) a first primer strand comprising (i) a 5' domain that comprises deoxyribonucleotides interspersed with ribonucleotides, and (ii) a 3' domain, optionally wherein the first primer comprises a stopper located between the 5' domain and the 3' domain, and (b) a template strand comprising a 3' domain that is complementary to the 3' domain of the first primer strand; incubating the reaction mixture under conditions that result in DNA polymerization to produce a first double-stranded nucleic acid; incubating the first double-stranded nucleic acid in reaction buffer that contains ribonuclease H (RNase H) under conditions that result in enzymatic cleavage of the first double-stranded nucleic acid to produce a first partially double-stranded nucleic acid comprising a toehold domain that is complementary to the 5' domain of the first primer strand; and incubating the partially double-stranded nucleic acid in reaction buffer in the presence of the first primer strand and strand-displacing polymerase under conditions that result in DNA polymerization to produce a second double-stranded nucleic acid, thereby displacing one strand of the first double-stranded nucleic acid.

Also provided herein, in some aspects, are compositions comprising (a) a strand-displacing polymerase, (b) a first primer strand comprising (i) a 5' domain that comprises deoxyribonucleotides interspersed with ribonucleotides, and (ii) a 3' domain, optionally wherein the first primer comprises a stopper located between the 5' domain and the 3' domain, and (c) a template strand comprising a 3' domain that is complementary to the 3' domain of the first primer strand. In some embodiments, compositions comprise (a) a strand-displacing polymerase and (b) a partially double-stranded nucleic acid comprising a first strand bound to a second strand and a third strand, wherein the second strand comprises (i) a 5' domain comprising deoxyribonucleotides interspersed with ribonucleotides that is homologous to and bound to a first 3' subdomain of the first strand and (ii) a 3' domain that is complementary to and bound to a second 3' subdomain of the first strand (wherein the second 3' subdomain of the first strand is upstream from the first 3' subdomain of the first strand), and wherein the third strand comprises (i) a 5' domain that is complementary to the second 3' subdomain of the first strand and is the same as the 3' domain of the second strand and (ii) a 3' domain that is complementary to and bound to a 5' domain of the first strand. In some embodiments, the compositions further comprise RNaseH.

Yet other aspects of the present disclosure provide, methods of producing a nucleic acid comprising: combining in reaction buffer that contains a strand-displacing polymerase (a) a first template strand comprising a 5' domain and a 3' domain, (b) a second template strand comprising a 5' domain and a 3' domain, (c) a first primer strand that comprises (i) a 5' domain that comprises deoxyribonucleotides interspersed with ribonucleotides, and (ii) a 3' domain, wherein the 3' domain of the first primer strand is complementary to the 3' domain of the second template strand, and optionally wherein the first primer strand comprises a stopper located between the 5' domain and the 3' domain, and (d) a second primer strand that comprises (i) a 5' domain that comprises deoxyribonucleotides interspersed with ribonucleotides, and (ii) a 3' domain, wherein the 3' domain of the second primer strand is complementary to the 3' domain of the first template strand, and optionally wherein the first primer strand comprises a stopper located between the 5' domain and the 3' domain; incubating the reaction mixture under conditions that result in DNA polymerization to produce double-stranded nucleic acids; and incubating the double-stranded nucleic acids in reaction buffer that contains ribonuclease H (RNase H) under conditions that result in enzymatic cleavage of the double-stranded nucleic acids.

Still other aspects of the present disclosure provide methods of producing a nucleic acid comprising: combining in reaction buffer that contains non-strand-displacing polymerase with reverse transcriptase activity (a) a template strand comprising in the 5' to 3' orientation a first domain, a second domain, a third domain, and a fourth domain, wherein the first domain and the third domain are complementary to and bound to each other, and wherein a stopper is located between the first domain and the second domain, and (b) a primer strand comprising in the 5' to 3' orientation a first domain and a second domain, wherein the first domain of the primer strand is complementary fourth domain of the template strand, and wherein the second domain of the primer strand is complementary to the third domain of the template strand; and incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid.

Some aspects further provide methods of molecular landscape probing comprising: combining in reaction buffer that contains polymerase (a) a substrate comprising a plurality of nucleic acids, wherein each nucleic acid comprises (i) a 5' domain that comprises deoxyribonucleotides interspersed with ribonucleotides, and (ii) a 3' domain, and wherein each nucleic acid is attached to the substrate through its 5' domain, and (b) a primer strand that is complementary to at least one 3' domain of a nucleic acid of the plurality; incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid.

Yet other methods provided herein comprise combining in reaction buffer that contains strand-displacing polymerase (a) a template strand comprising at least one ribonucleotide adjacent to a stopper separating a 5' domain from a 3' domain, and (b) a primer strand comprising a domain that is complementary to the 3' domain of the template strand; incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid.

BRIEF DESCRIPTION OF DRAWINGS

FIG. 7A shows how primers can be programmed to modify surface-tethered oligonucleotides. FIG. 7B shows how primers can be used to record in their sequences information about the surfaces they contact/modify. FIG. 7C shows how primers can 'crawl' along molecular landscapes, recording interactions, by traversing irreversibly from one molecule (e.g., oligonucleotide) to another.

FIG. 11A shows reaction diagrams for a one-step reaction to append the domains b and c onto a primer ending in domain a using a chimeric template strands of the form c* b* a*. The circle indicates an RNA base. FIG. 11B shows templates using one ($T_1R_1$) and two ($T_1R_2$) RNA bases (indicated by circles) intercalated under four different reaction conditions (with primer ($R_1$ and $R_2$) and with primer and an additional extension template ($R_3$ and $R_4$)). FIG. 11C shows the resulting gel from the templates depicted in FIG. 11B. FIG. 11D shows the templates of FIG. 11B subjected to three other reaction conditions: with no enzymes ($C_1$), with the polymerase ($C_2$), and with both the polymerase and RNase H2 enzyme ($C_3$). Note that the wells for each condition, from left to right, correspond to reaction conditions $R_1$-$R_4$ as illustrated in FIG. 11B.

DESCRIPTION

Provided herein are compositions, methods and kits for the dynamic, isothermal and autonomous production of single-stranded and double-stranded DNA transcripts for use in, for example, isothermal exponential amplification reactions, ultraspecific target detection assays, kinetic proofreading assays, and molecular assembling and recording reactions. Other applications are contemplated herein.

Programmable Nucleic Acid Synthesis Cascade

Figure 1A:
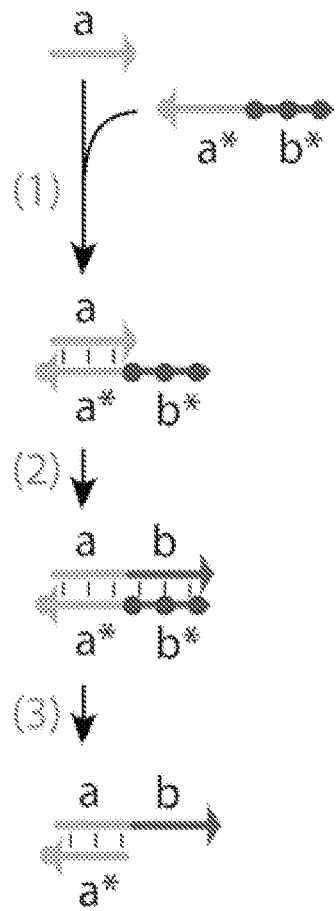
FIGS. 1A and 1B show reaction diagrams for example basic reactions to append domain 'b' onto a (nucleic acid) primer ending in domain 'a', using chimeric template (nucleic acid) strands of the form 'b* a*'.
Figure 1B:
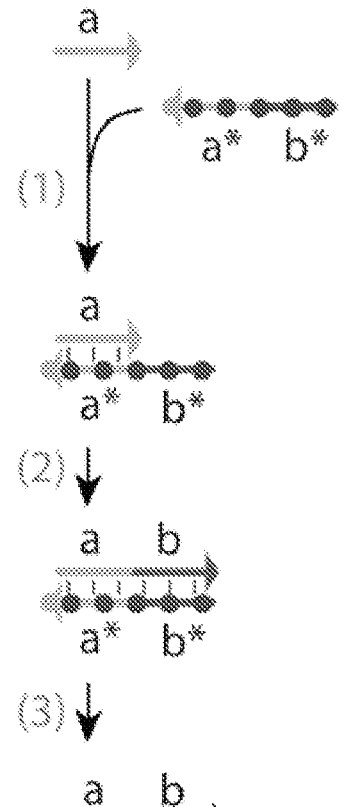

An example of a basic programmable nucleic acid synthesis cascade is depicted in FIGS. 1A-1B. This method combines DNA polymerization with RNA digestion to synthesize single-stranded and double-stranded DNA isothermally.

The synthesis cascade has three main steps (FIGS. 1A and 1B). First, a primer strand (a) binds to a cognate template sequence (first nucleic acid strand) (b* a*) (step 1). The template strand (first nucleic acid strand) contains deoxyribonucleotides interspersed (intercalated) with ribonucleotides. In step 2, a DNA polymerase copies out the next domain onto the primer, resulting in a double-stranded RNA/DNA hybridized portion. Then, the RNA bases in the newly created RNA/DNA hybridized portion are cleaved by an RNase H enzyme (step 3). In FIG. 1A, the 5'-most domain of the template contains interspersed (intercalated) RNA bases so that it may be digested by an RNase H enzyme once the b sequence has been copied onto the primer. In contrast, FIG. 1B depicts a situation where the RNA bases are interspersed (intercalated) throughout the template sequence, so that when it is cleaved, the primer strand is left single-stranded.

Figure 1C:
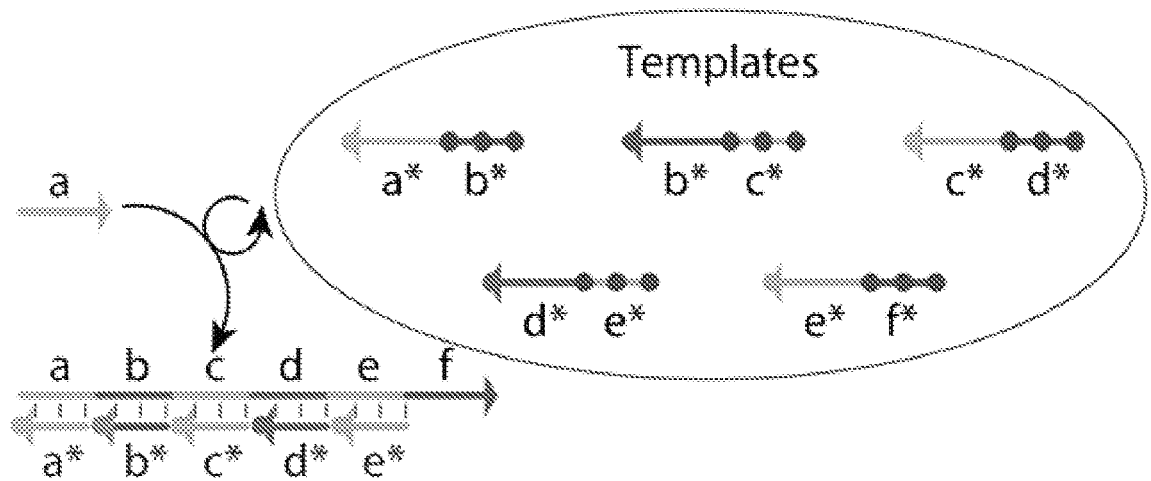
FIGS. 1C and 1D show how several template strands can be pooled together to program the autonomous growth of a primer sequence through a cascade of synthesis reactions. RNA bases are indicated by the dots incorporated along the strands.
Figure 1D:
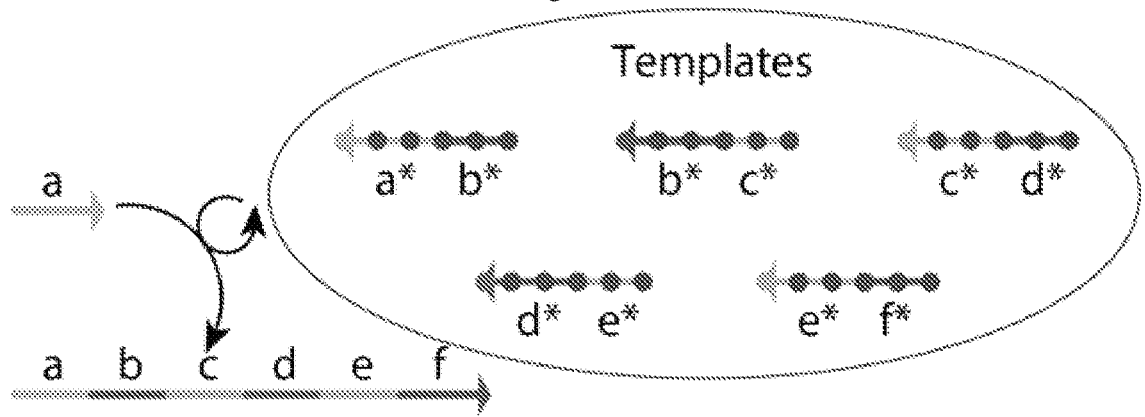

The synthesis cascades may be pooled together to program the autonomous growth of a primer sequence through a cascade of synthesis reactions: largely double-stranded (FIG. 1C) or largely single-stranded (FIG. 1D) DNA polymers can be synthesized depending on the template strategy used.

Primer Strands

A "primer strand" (also referred to simply as a "primer") is a nucleic acid that, when bound to another nucleic acid, is the starting point for polymerization in the presence of a polymerase. As used herein, a primer is typically a nucleic acid (e.g., single-stranded nucleic acid) having a deoxyribonucleotide sequence, a ribonucleotide sequence, or a mixed deoxyribonucleotide/ribonucleotide sequence that is complementary to nucleotides of a template strand (see, e.g., strand a, primer and strand b* a*, template of FIG. 1A). Thus, a "template strand" is a nucleic acid to which a primer binds. A template strand comprises a domain that is complementary to a domain of the primer ("template strand domain").

It should be understood that the term "complementary" encompasses complementarity between deoxyribonucleotides, complementarity between ribonucleotides, and complementarity between deoxyribonucleotides and ribonucleotides. For example, a primer strand having the DNA sequence 5'-ATCGTACG-3' is considered complementary to a template strand having the DNA sequence 5'-CGTACGAT-3'. Likewise, a primer strand having the DNA sequence 5'-ATCGTACG-3' is considered complementary to a template strand having the RNA sequence 5'-CGUACGAU-3'. Thus, A is complementary to T and U, and C is complementary to G.

Figure 7A:
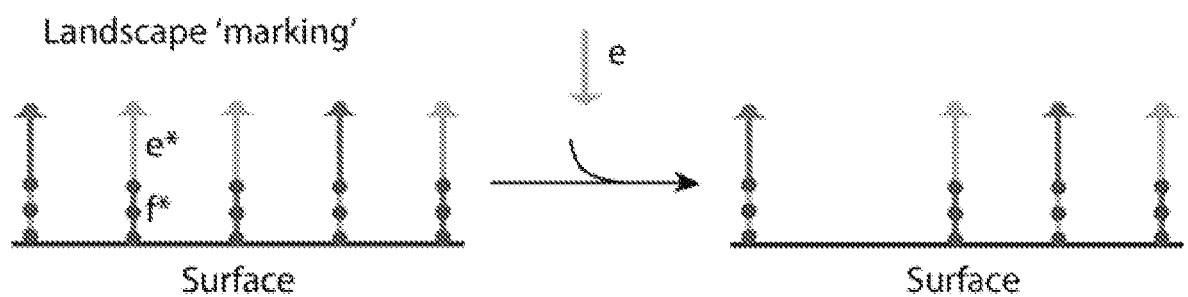
FIGS. 7A-7C show examples of molecular landscaping methods using mixed DNA/RNA nucleic acids.
Figure 7B:
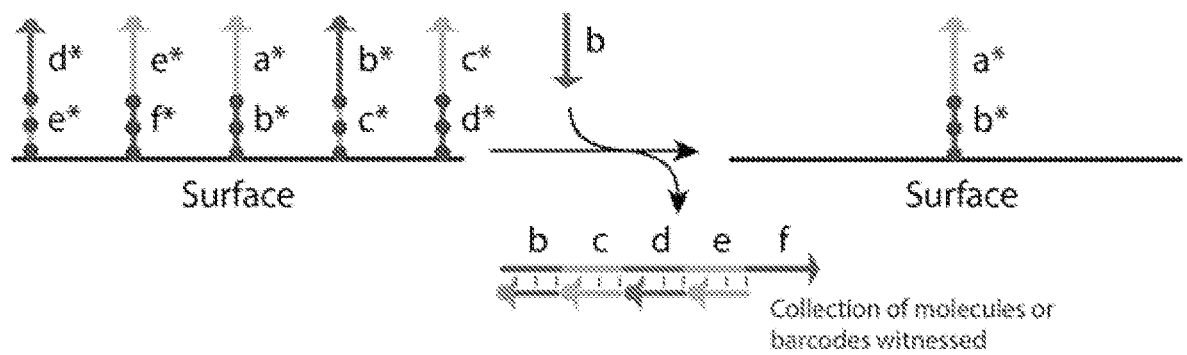

It should also be understood that nucleic acids or nucleic acid domains are considered "homologous" to each other if the two nucleic acids or nucleic acid domains have the same nitrogenous base composition (e.g., same bases but different sugars). For example, as shown in FIG. 7B, domain c*, containing interspersed ribonucleotides and deoxyribonucleotides (e.g., 5'-AUCGTAUCG-3'), is considered homologous to domain c*, containing only deoxyribonucleotides (5'-ATCGTATCG-3').

A "domain" refers to a discrete, contiguous sequence of nucleotides or nucleotide base pairs, depending on whether the domain is unpaired (single-stranded nucleotides) or paired (double-stranded nucleotide base pairs), respectively.

In some embodiments, a domain is described as having multiple subdomains for the purpose of defining intramolecular (within the same molecular species) and intermolecular (between two separate molecular species) complementarity. One domain (or one subdomain) is "complementary to" another domain if one domain contains nucleotides that base pair (hybridize/bind through Watson-Crick nucleotide base pairing) with nucleotides of the other domain such that the two domains form a paired (double-stranded) or partially-paired molecular species/structure. Complementary domains need not be perfectly (100%) complementary to form a paired structure, although perfect complementarity is provided, in some embodiments. Thus, a primer that is "complementary" to a particular domain binds to that domain, for example, for a time sufficient to initiate polymerization in the presence of polymerase.

The term "primer" encompasses primers that are 100% complementary to a target domain as well as "primer domains"—the nucleotide sequence within a primer strand that binds to a complementary domain of a template strand.

A primer, in some embodiments, comprises nucleotides that consist of deoxyribonucleotides or ribonucleotides. In other embodiments, a primer comprises a mixture of deoxyribonucleotides and ribonucleotides. In some embodiments, a primer comprises a mixture of different nucleotides. Thus, in some embodiments, a primer comprises deoxyribonucleotides, ribonucleotides, modified deoxyribonucleotides, modified ribonucleotides, methylated ribonucleotides, peptide ribonucleotides (PNA), locked nucleotides (LNA), or any combination thereof. In some embodiments, a primer comprises a mixture of deoxyribonucleotides and ribonucleotides. In some embodiments, the primer comprises 30%, 35%, 40%, 45%, 50%, 55%, 60%, 65%, 70%, 75%, 80%, 85%, 90%, 95%, 96%, 97%, 98%, or 99% deoxyribonucleotides, and the remainder of the primer comprises ribonucleotides. In some embodiments, the primer comprises 30%, 35%, 40%, 45%, 50%, 55%, 60%, 65%, 70%, 75%, 80%, 85%, 90%, 95%, 96%, 97%, 98%, or 99% ribonucleotides, and the remainder of the primer comprises deoxyribonucleotides. In some embodiments, the primer comprises at least one (e.g., 1, 2, 3, 4, 5, or more) deoxyribonucleic acid (comprises less than 100% ribonucleotides). In some embodiments, the primer comprises at least one (e.g., 1, 2, 3, 4, 5, or more) ribonucleic acid (comprises less than 100% deoxyribonucleotides).

It should be understood that a primer or a template that comprises deoxyribonucleotides "interspersed" with ribonucleotides encompasses a patterned (e.g., alternating) or random mixture of deoxyribonucleotides and ribonucleotides.

In some embodiments, the mixed nucleotides along a primer are evenly spaced relative to one another; for example, a ribonucleotide may follow every other deoxyribonucleotide, every two deoxyribonucleotides, every three deoxyribonucleotides, and so on. Thus, in some embodiments, the interspersed (intercalated) nucleotides in the primer comprise a ribonucleotide every other, or every 2, 3, 4, 5, 6, 7, 8, 9, or 10 deoxyribonucleotides. In other embodiments, the mixed nucleotides are not evenly spaced, but rather are randomly mixed along the length of the primer.

In some embodiments, a primer has a length of 10-50 nucleotides. For example, a primer may have a length of 10-45, 10-40, 10-35, 10-30, 10-25, 10-20, 10-15, 15-50, 15-45, 15-40, 15-35, 15-30, 15-25, 15-20, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a primer has a length of 10, 15, 20, 25, 30, 35, 40, 45 or 50 nucleotides. In some embodiments, a primer has a length of 15, 16, 17, 18, 19, 20, 21, 22, 23, 24 or 25 nucleotides. A primer, in some embodiments, is longer than 50 nucleotides, or shorter than 10 nucleotides.

In some embodiments, a primer comprises a detectable label, such as a fluorophore or other label, as discussed below.

Template Strand

A "template strand," as discussed above, is a nucleic acid to which a primer binds. A template strand comprises a domain that is complementary to a domain of the primer ("template domain"). In some embodiments, the template domain spans the entire length of the template strand (thus, the primer binds along the entire length of the template strand). In other embodiments, the template domain is contiguous with adjacent or flanking nucleotides that are not complementary to a primer domain (thus, the primer binds to only a portion of the template strand). In some embodiments, the template strand may be "self-hybridized" (e.g., two domains of the same strand bound to each other) to form a hairpin structure.

A template, in some embodiments, comprises nucleotides that consist of deoxyribonucleotides or ribonucleotides. In other embodiments, a template comprises a mixture of deoxyribonucleotides and ribonucleotides. In some embodiments, a template comprises a mixture of different nucleotides. That is, one type of nucleotide (e.g., RNA) may be interspersed (intercalated) with one or more other types of nucleotide (e.g., DNA). Thus, in some embodiments, a template comprises deoxyribonucleotides, ribonucleotides, modified deoxyribonucleotides, modified ribonucleotides, methylated ribonucleotides, peptide ribonucleotides (PNA), locked nucleotides (LNA), or any combination thereof. In some embodiments, a template comprises a mixture of deoxyribonucleotides and ribonucleotides. In some embodiments, the template comprises 30%, 35%, 40%, 45%, 50%, 55%, 60%, 65%, 70%, 75%, 80%, 85%, 90%, 95%, 96%, 97%, 98%, or 99% deoxyribonucleotides, and the remainder of the template comprises ribonucleotides. In some embodiments, the template comprises 30%, 35%, 40%, 45%, 50%, 55%, 60%, 65%, 70%, 75%, 80%, 85%, 90%, 95%, 96%, 97%, 98%, or 99% ribonucleotides, and the remainder of the template comprises deoxyribonucleotides. In some embodiments, the template comprises at least one (e.g., 1, 2, 3, 4, 5, or more) deoxyribonucleic acid (comprises less than 100% ribonucleotides). In some embodiments, the template comprises at least one (e.g., 1, 2, 3, 4, 5, or more) ribonucleic acid (comprises less than 100% deoxyribonucleotides).

In some embodiments, the mixed nucleotides along a template are evenly spaced relative to one another; for example, a ribonucleotide may follow every other deoxyribonucleotide, every two deoxyribonucleotides, every three deoxyribonucleotides, and so on. Thus, in some embodiments, the interspersed (intercalated) nucleotides in the template comprise a ribonucleotide every other, or every 2, 3, 4, 5, 6, 7, 8, 9, or 10 deoxyribonucleotides. In other embodiments, the mixed nucleotides are not evenly spaced, but rather are randomly mixed along the length of the template.

In some embodiments, a template strand (or any other nucleic acid as provided herein) has a length of 10-100 nucleotides. For example, a template strand (or any other nucleic acid as provided herein) may have a length of 10-95, 10-90, 10-85, 10-80, 10-75, 10-70, 10-65, 10-60, 10-65, 10-50, 10-45, 10-40, 10-35, 10-30, 10-25, 10-20, 10-15, 15-100, 15-95, 15-90, 15-85, 15-80, 15-75, 15-70, 15-65, 15-60, 15-55, 15-50, 15-45, 15-40, 15-35, 15-30, 15-25, 15-20, 20-100, 20-95, 20-90, 20-85, 20-80, 20-75, 20-70, 20-65, 20-60, 20-55, 20-50, 20-45, 20-40, 20-35, 20-30, 20-25, 25-50, 25-45, 25-40, 25-35, 25-30, 30-50, 30-45, 30-40, 30-35, 35-50, 35-45, 35-40, 40-50, 40-45 or 45-50 nucleotides. In some embodiments, a template strand (or any other nucleic acid as provided herein) has a length of 10, 15, 20, 25, 30, 35, 40, 45, 50, 60, 70, 80, 90 or 100 nucleotides. A template strand (or any other nucleic acid as provided herein), in some embodiments, is longer than 100 nucleotides, or shorter than 10 nucleotides. In some embodiments, the template strand domain is long enough so that the template strand remains bound to its complementary primer. In other embodiment, the template strand domain is short enough for spontaneous dissociation from its complementary primer. In some embodiments, the template strand domain does not contain a genetic element, such as a promoter.

In some embodiments, the template includes a 3' modification or sequence to inhibit extension by a polymerase (referred to as a "stopper"). In some embodiments, the stopper is located on the 3' end of the template. In some embodiments, the stopper is located within a template, flanked by nucleotides. In some embodiments, a stopper is located immediately upstream (5') from a ribonucleotide present in the template. In some embodiments, the molecule that terminates polymerization is a synthetic non-DNA linker, for example, a short triethylene glycol spacer, such as the Int Spacer 9 (iSp9) or Spacer 18 (Integrated DNA Technologies (IDT)). It should be understood that any non-native linker that terminates polymerization by a polymerase may be used. Other non-limiting examples of such molecules and modifications include a three-carbon linkage (/iSpC3/) (IDT), 1',2'-dideoxyribose (dSpacer), ACRYDITE™ (IDT), adenylation, azide, digoxigenin (NHS ester), cholesteryl-TEG (IDT), I-LINKER™ (IDT), and 3-cyanovinylcarbazole (CNVK) and variants thereof. Typically, but not always, short linkers (e.g., iSp9) lead to faster reaction times.

In some embodiments, the molecule that terminates polymerization is a single or paired non-natural nucleotide sequence, such as iso-dG and iso-dC (IDT), which are chemical variants of cytosine and guanine, respectively. Iso-dC will base pair (hydrogen bond) with iso-dG but not with dG. Similarly, iso-dG will base pair with iso-dC but not with dC. By incorporating these nucleotides, the polymerase will be halted, as it does not have a complementary nucleotide in solution to add at that position.

In some embodiments, RNA bases and/or methylated RNA bases, for example, a sequence of one or more 2'-O-methyl RNA bases, may be used as stoppers.

In some embodiments, the efficiency of performance of a "stopper" modification is improved by lowering dNTP concentrations (e.g., from 200 µM) in a reaction to 100 µM, 10 µM, 1 µM, or less.

Figure 10A:
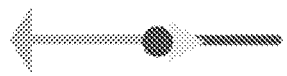
FIG. 10A shows another example design of a chimeric strand. At least one RNA base (indicated by a circle) is incorporated in the middle of the strand, for cleavage by RNase H. Immediately preceding this cleavage site is a modification or sequence that cannot be extended by a polymerase (indicated by a triangle).

A schematic of a chimeric template with a stopper (unextendable portion) is provided in FIG. 10A. The chimeric template comprises at least one RNA base (indicated by a circle) toward the middle of the strand. The at least one RNA base can be cleaved by an RNase. The modification or sequence that cannot be extended by a polymerase (depicted as a triangle) is located immediately following the cleavage site. In some embodiments, following RNase cleavage, the chimeric template may serve as a primer through its unprotected 3' end.

A template, in some embodiments, is linked to (labeled with) a detectable molecule (e.g., a molecule that emits a detectable signal, such as a fluorescent or chemiluminescent signal). In some embodiments, the label is a fluorophore. A template linked to a fluorophore or other fluorescent/chemiluminescent molecule is referred to simply as a "fluorescent template." Examples of fluorophores that may be used herein include, without limitation, hydroxycoumarin, methoxycoumarin, Alexa fluor, aminocoumarin, Cy2, FAM, Alexa fluor 405, Alexa fluor 488, Fluorescein FITC, Alexa fluor 430, Alexa fluor 532, HEX, Cy3, TRITC, Alexa fluor 546, Alexa fluor 555, R-phycoerythrin (PE), Rhodamine Red-X, Tamara, Cy3.5 581, Rox, Alexa fluor 568, Red 613, Texas Red, Alexa fluor 594, Alexa fluor 633, Allophycocyanin, Alexa fluor 647, Cy5, Alexa fluor 660, Cy5.5, TruRed, Alexa fluor 680, Cy7 and Cy7.5. Other fluorophores and molecules that emit a detectable signal are encompassed by the present disclosure.

In some embodiments, a template strand is linked to a biomolecule. Biomolecules include, for example, nucleic acids (e.g., DNA and RNA) and proteins (including peptides). A biomolecule may be a therapeutic, prophylactic, diagnostic or imaging molecule. In some embodiments, a biomolecule is a disease-related or drug-related biomolecule, such as a cancer-related gene or protein, or an FDA-approved or potential drug target. In some embodiments, a biomolecule is an enzyme, an antibody, an antigen, a receptor, a ligand, a membrane protein, a secreted protein, or a transcription factor.

Polymerase

A synthesis cascade of the present disclosure uses a polymerase having reverse transcriptase activity. In some embodiments, the polymerase is a DNA polymerase (DNAP). In other embodiments, the polymerase has strand-displacing activity (a strand displacement polymerase). In other embodiments, the polymerase does not have strand-displacing activity (a non-strand-displacing polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB # M0269), Bst DNA polymerase, large fragment (e.g., NEB # M0275), or Bsu DNA polymerase, large fragment (e.g., NEB # M0330). Other polymerases having strand displacement activity may be used.

In some embodiments, the polymerase used is characterized simply by its ability to catalyze polymerization of nucleotides into a nucleic acid strand, including thermostable polymerases and reverse transcriptases (RTases). Examples include *Bacillus stearothermophilus* pol I, *Thermus aquaticus* (Taq) pol I, *Pyrccoccus furiosus* (Pfu), *Pyrococcus woesei* (Pwo), *Thermus flavus* (Tfl), *Thermus thermophilus* (Tth), *Thermus litoris* (Tli) and *Thermotoga maritime* (Tma). These enzymes, modified versions of these enzymes, and combination of enzymes, are commercially available from vendors including Roche, Invitrogen, Qiagen, Stratagene, and Applied Biosystems. Representative enzymes include PHUSION® (New England Biolabs, Ipswich, Mass.), Hot MasterTaq™ (Eppendorf), PHUSION®

Mpx (Finnzymes), PyroStart® (Fermentas), KOD (EMD Biosciences), Z-Taq (TAKARA), and CS3AC/LA (KlenTaq, University City, Mo.).

In some embodiments, the polymerase is a RNA polymerase (RNAP).

Ribonuclease

The synthesis cascade of the present disclosure requires a ribonuclease (RNase) that specifically cleaves RNA bases bound in an RNA-DNA hybrid, but does not cleave single-stranded RNA. For example, RNase H (ribonuclease H) is a family of non-sequence specific endonuclease enzymes which use hydrolysis to catalyze the cleavage of RNA in an RNA-DNA hybrid. Examples of such RNases include RNase HII (NEB) and RNase H2 (IDT).

Isothermal Exponential Amplification

Figures 2A, 2B:
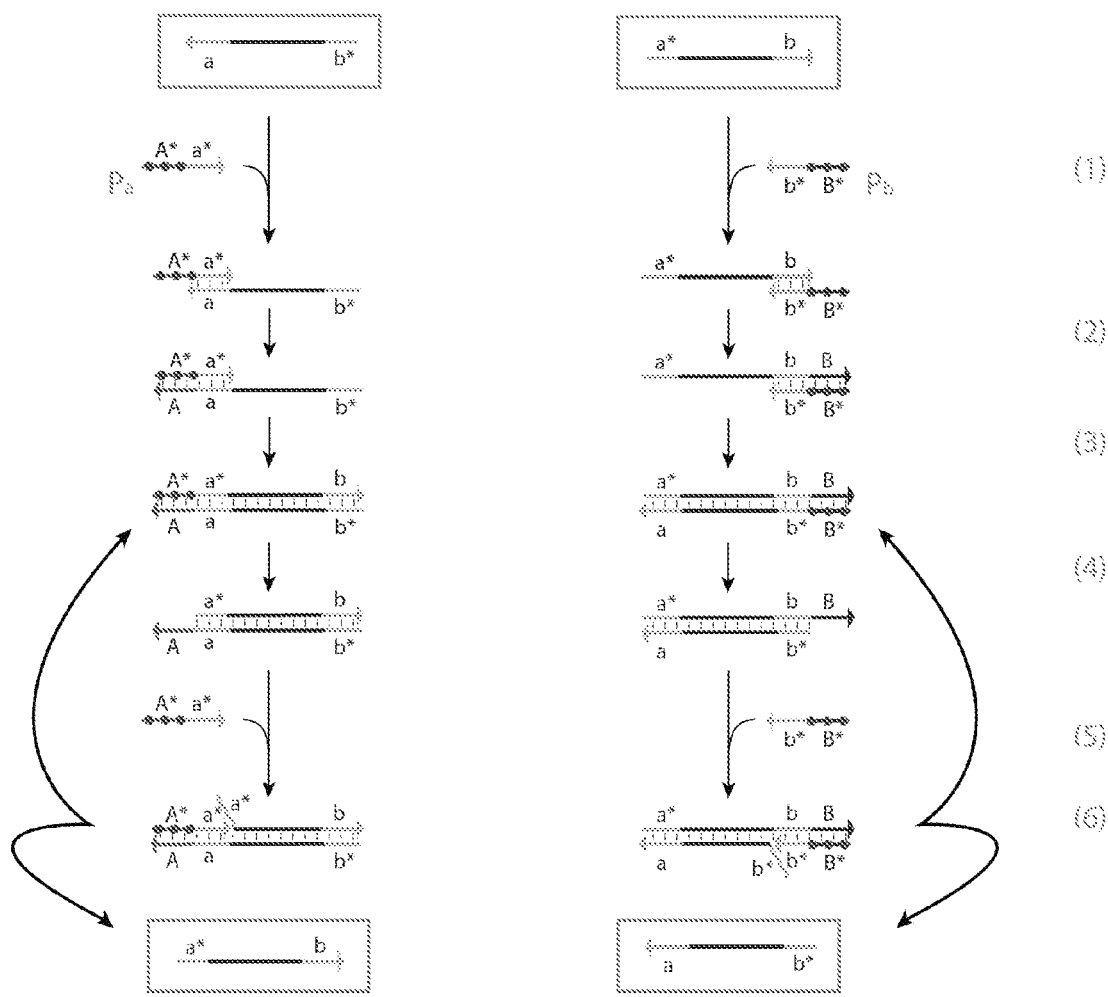
FIG. 2A shows a reaction schematic for producing many copies of a target strand flanked by 5' domain 'a*' and 3' domain 'b', starting with a complement template strand flanked by 5' domain 'b*' and 3' domain 'a'.
FIG. 2B shows a reaction schematic for producing many copies of a target strand flanked by 5' domain 'b*' and 3' domain 'a', starting with a complement template strand flanked by 5' domain 'a*' and 3' domain 'b'.

The present disclosure, in some aspects, provides a method for exponentially amplifying a target amplicon. Examples of isothermal exponential amplification reactions are shown in FIGS. 2A-2B. FIG. 2A shows how an amplicon sequence flanked by primer regions b* (on the 5' side) and a (3') produces many copies of the complement of the target flanked by a* and b using a single chimeric primer (Pa). Similarly, FIG. 2B shows how the targets flanked by a* and b can produce many copies of the strands flanked by b* and a using the chimeric Pb primer.

These reaction cascades occur in several steps. A chimeric primer (e.g., having a mixture of deoxyribonucleotide and ribonucleotides) first binds to the target (step 1). Then the target copies the complement of the RNA-intercalated region using a polymerase with reverse transcriptase activity, and the primer copies the target amplicon sequence (steps 2 and 3). An RNase cleaves the ribonucleotide-intercalated domain from the copied deoxyribonucleotide sequence (A* in FIG. 2A and B* in FIG. 2B) to expose a toehold for the next primer to bind (step 4). Another primer can then bind on this exposed toehold and displace through the complementary region (step 5), so that a strand displacing DNA polymerase can make a copy of the target and displace the original copy (step 6). This original copy is then replicable, and the new double-stranded amplicon created from the second primer binding can be cycled through another cleavage reaction.

Figure 3:
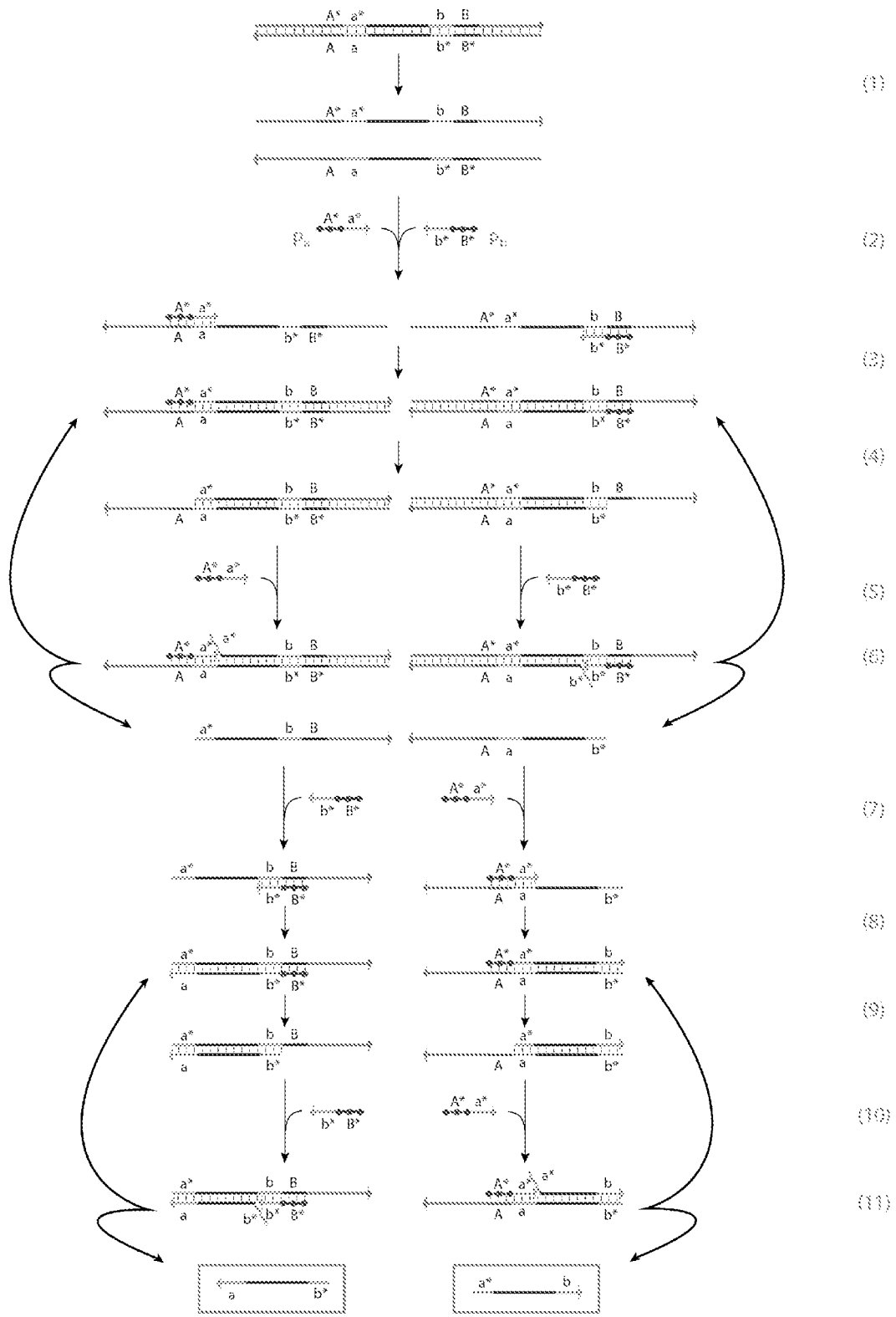
FIG. 3 shows an example of a method of amplifying a double-stranded target. Following denaturation of a double-stranded target, two primers ($P_a$ and $P_b$) facilitate the exponential amplification of the region between the 'a' and 'b' primer domains.
Figure 4:
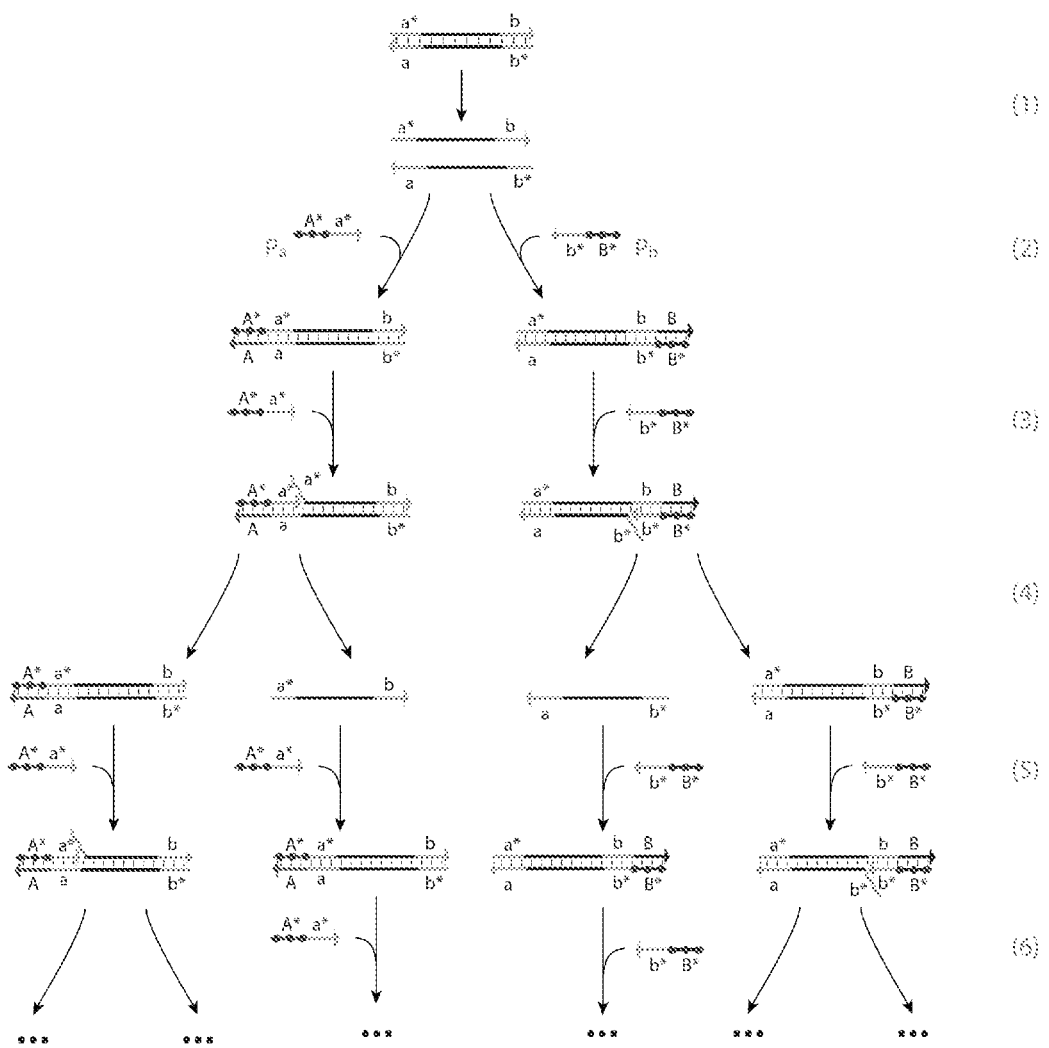
FIG. 4 shows an example of a method of amplifying a double-stranded amplicon. The strategy is similar to that of FIG. 3, but using a different diagrammatic format.

The same two primers can be used to replicate a target amplicon region within a double-stranded target (FIG. 3). First, the double-stranded target is denatured, typically through a heating step (step 1). Then, the Pa and Pb primers can bind to the strands and copy out the amplicon regions (steps 2 and 3). The same type of cleavage reaction as described in FIGS. 2A-2B is then capable of exposing the A and B regions so that more primers can bind, displace, and copy the amplicon region and in the process displace a single-stranded copy (steps 4-6). These single-stranded copies are also replicated in a similar process with the two primers, Pa and Pb (steps 7-10). Additional primers may be used. In some embodiments, 3, 4, 5, 6, 7, 8, 9, or 10 primers are used. Ultimately, as amplicon copies grow exponentially, copies of the form depicted in FIGS. 2A-2B dominate the amplification reactions. FIGS. 3 and 4 show a similar process using a double-stranded target and amplicon, respectively, as the starting template.

Figure 10B:
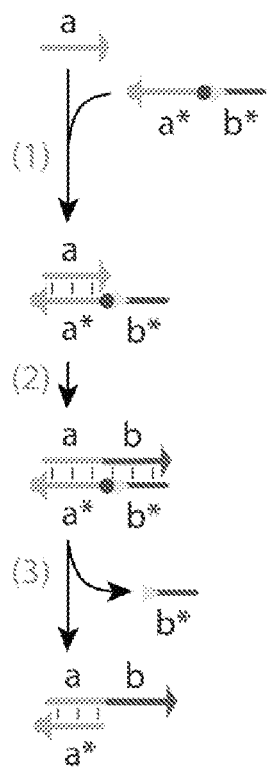
FIG. 10B shows the reaction diagram for a basic reaction to append the domain b onto a primer ending in domain a using a chimeric template strand of the form b* a*.
Figure 10C:
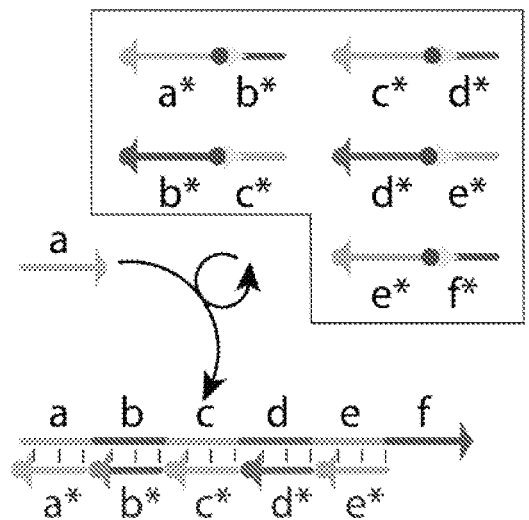
FIG. 10C shows how several template strands can be pooled together to program the autonomous growth of a primer sequence through a cascade of synthesis reactions.

FIG. 10B shows a similar process using a chimeric template strand comprising a stopper modification or sequence. The reaction proceeds as described above, and when the chimeric template strand is cleaved from the target amplicon, it can serve as a primer (through its unprotected 3' end) in a further reaction. As shown in FIG. 10C, multiple chimeric template strands may be pooled together to program the autonomous growth of a primer sequence through a cascade of synthesis reactions.

Ultraspecific Target Detection

In addition to amplification, the RNase H-aided strand synthesis cascade can also be used to implement a kinetic proofreading scheme for ultraspecific specific target detection. Typically, simple competitive hybridization reactions are limited in their ability to discriminate between correct and incorrect targets due to the limit on discrimination imposed by their different binding thermodynamics. Nonetheless, specificity of such reactions can be improved if target sequences are checked at each of a series of irreversible reaction steps through a process referred to as kinetic proofreading (Hopfield, *PNAS* (1974) 71(10):4135-9).

Figure 5A:
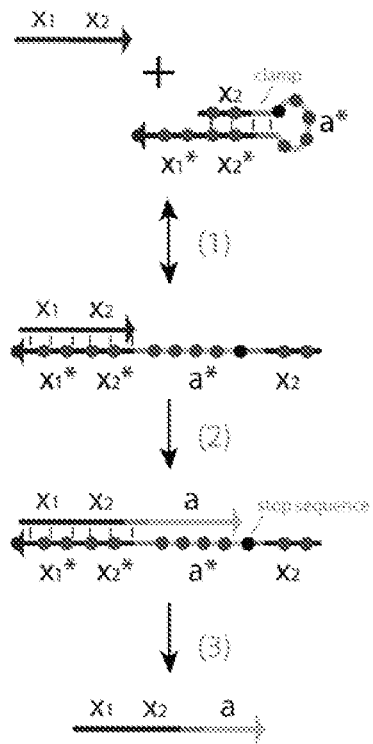
FIG. 5A shows how a target sequence of the form 'x1 x2' can be verified ('proofread') through hairpin binding, displacement, and synthesis reactions.
Figure 5B:
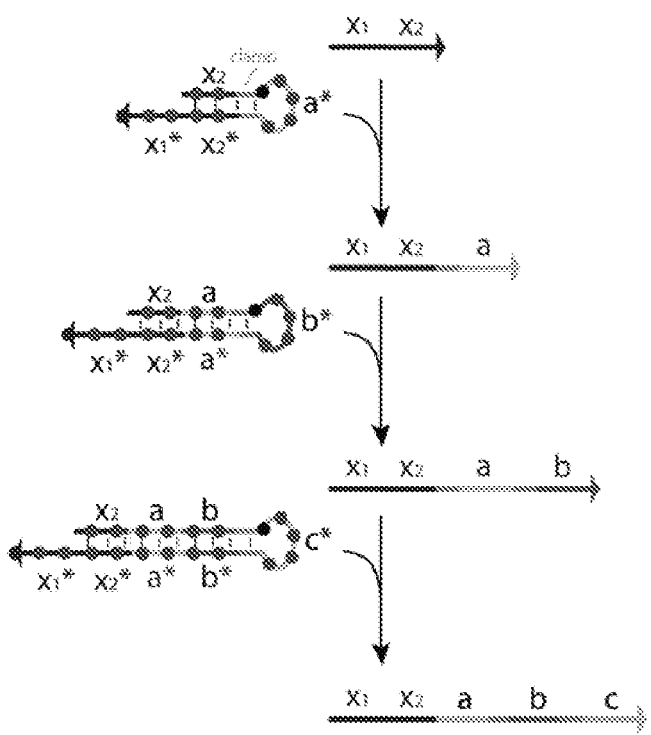
FIG. 5B shows how several verification steps can be cascaded together to further proofread a sequence.

RNase H-aided strand synthesis cascades of the present disclosure can be used for kinetic proofreading, by appending domains to a target sequence at each of several pre-scribed "checkpoints" (FIGS. 5A-5B). An example of a basic elongation method is depicted in FIG. 5A. First, a target binds to a hairpin on the complementary x1* toehold and then displaces through the x2 region (step 1). A "hairpin" structure is a stretch of contiguous nucleotides that folds through intramolecular base pairing to form a paired domain flanked by a unpaired linear domain and an unpaired loop domain, as shown, for example, in FIG. 5A ("a*"). This process is reversible and highly discriminative toward correct target sequences, as mismatched sequences are very unlikely to successfully displace the full x2 domain. Only once the strand has fully displaced through the hairpin can a non-strand-displacing polymerase with reverse transcriptase activity append the a domain directly onto the target (step 2). The hairpin portion bound to the elongated primer is then digested by RNase H, which exposes the new x1 x2 a sequence (step 3). There is an additional 'clamp' domain included in the stem and copied between the x2 and a domains whose length can be adjusted to increase the specificity of the reaction. The 'clamp' domain may be of any length, including 0 base pairs.

Arbitrary numbers of these reactions can be cascades to further increase the specificity of on-versus off-target detection. FIG. 5B shows such a cascade, where three checking steps are performed. The number of checking steps may be, for example, 1, 2, 3, 4, 5, 6, 7, 8, 9, 10, or greater. Ultimately, the target will be accepted when n domains have been appended, where n is a number chosen based on desired specificity of the detection. The final product produced by the last elongation step may be PCR amplified using the final appended domain (c in the case of FIG. 5B) as the binding site for one of the PCR primers.

Thus, in some embodiments, a target strand forms a hairpin structure, which is a stretch of contiguous nucleotides that folds through intramolecular base pairing to form a paired domain flanked by an unpaired linear domain and an unpaired loop domain, as shown, for example, in FIGS. 5A and 5B. While "hairpins" generally contain a loop domain, it should be understood that any hairpin may be substituted with any nucleic acid duplex that includes a 3' unpaired domain and an adjacent 5' paired domain.

An "unpaired domain" of a nucleic acid refers to a sequence of nucleotides that is not bound to a complementary sequence of nucleotides. Single-stranded nucleic acids, for example, are considered "unpaired" nucleic acids. Hairpin primers generally include a 3' unpaired domain that is complementary to (and binds to) a primer domain. The length of a 3' unpaired domain (or the length of any other domain of a hairpin molecule) may vary. In some embodiments, a 3' unpaired domain has a length of 5-40 nucleotides. For example, a 3' unpaired domain may have a length of 2-35, 2-30, 2-25, 2-20, 2-15, 2-10, 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a 3' unpaired domain has a length of 5, 10, 15, 20, 25, 30, 35 or 40 nucleotides. In some embodiments, a 3' unpaired domain has a length of 10, 11, 12, 13, 14, 15, 16, 17, 18, 19, 20, 21, 22, 23, 24 or 25 nucleotides. A 3' unpaired domain, in some embodiments, is longer than 40 nucleotides, or shorter than 5 nucleotides.

A "paired domain" of a nucleic acid refers to a sequence of nucleotides bound to a complementary sequence of nucleotides (e.g., Watson-Crick nucleobase pairing). Double-stranded nucleic acids, for example, are considered "paired" nucleic acids. A paired domain of a hairpin is typically located 5' from (and, in some embodiments, directly adjacent to) the 3' unpaired domain. The paired domain of hairpin is formed by intramolecular base pairing (base pairing between nucleotides within the same molecule) of a single-stranded nucleic acid. The length of a paired domain may vary. In some embodiments, a paired domain has a length of 5-40 nucleotides. For example, a paired domain may have a length of 5-35, 5-30, 5-25, 5-20, 5-15, 5-10, 10-40, 10-35, 10-30, 10-25, 10-20, 10-15, 15-40, 15-35, 15-30, 15-25, 15-20, 20-40, 20-35, 20-30, 20-25, 25-40, 25-35, 25-30, 30-40, 30-35 or 35-40 nucleotides. In some embodiments, a paired domain has a length of 5, 10, 15, 20, 25, 30, 35 or 40 nucleotides. In some embodiments, a paired domain has a length of 10, 11, 12, 13, 14, 15, 16, 17, 18, 19, 20, 21, 22, 23, 24 or 25 nucleotides. A paired domain, in some embodiments, is longer than 40 nucleotides, or shorter than 5 nucleotides.

In some embodiments, a 5' paired domain has subdomains (e.g., two subdomains), as depicted, for example, in FIG. 5B.

A "loop domain" of a hairpin refers to an unpaired domain that form a loop-like structure at the end (adjacent to) a 5' paired domain. That is, a loop domain links complementary domains of a nucleic acid to form a 5' paired domain. The length of a loop domain may vary. In some embodiments, a loop domain has a length of 3 to 50 nucleotides. For example, a loop domain may have a length of 3, 4, 5, 6, 7, 8, 9 or 10 nucleotides. In some embodiments, a loop domain has a length of 3-10, 3-15, 32-10, 3-25, 3-30, 3-35, 3-40, 3-35, 3-40, 3-45, 3-50, 4-10, 4-15, 4-10, 4-25, 4-30, 4-35, 4-40, 4-35, 4-40, 4-45 or 4-50 nucleotides. In some embodiments, a loop domain is longer than 50 nucleotides.

In some embodiments, there is a paired domain located between the loop domain and a stopper sequence, which helps to keep hairpin structures more tightly closed.

Molecular Assembling and Recording

Programmable RNase H-mediated synthesis cascades also enable a number of other applications, ranging from fluorescent signal amplification to recorders and crawlers that traverse molecular landscapes.

Figure 6A:
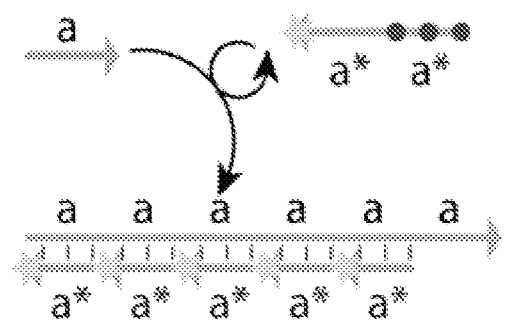
FIG. 6A shows an example of tethering fluorophores attached (e.g., directly attached) to chimeric templates along growing primer strands.
Figure 6B:
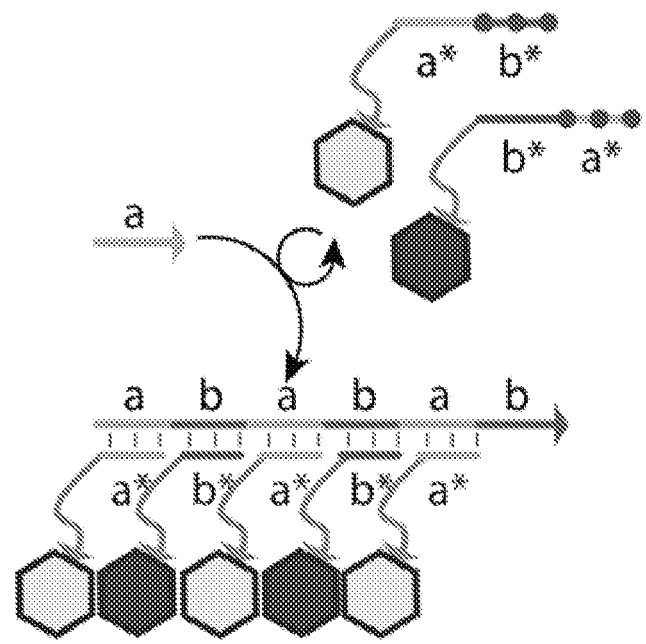
FIG. 6B shows an example of tethering other molecules attached (e.g., via a linker) to chimeric templates along growing primer strands.

Because some parts of the chimeric template strands can be preserved in the digestion process, and since these domains can be designed to be long enough to bind permanently to the growing strand, this provides the opportunity to attach molecules to a growing strand (FIGS. 6A-6B). For example, if fluorophores are included on the 3' end of a continuously growing template, then long concatemers of these fluorescent molecules can be created (FIG. 6A). Similarly, if other molecules such as proteins or antibodies are attached to the template strand, they can be tethered together in a programmable manner (FIG. 6B).

Because these polymers are assembled onto a growing primer strand, this construction may be used to grow these large fluorescent or macromolecular structures in crowded environments such as a fixed cell where it would be difficult for the large final polymer to diffuse easily. For example, the short a primer might be attached to a target molecule or surface, and then the structures could be synthesized directly in place. In some embodiments, the chimeric template strand may have an unextendable portion (the end that is released when the RNase cleaves the strand cannot be extended by a polymerase) (FIGS. 10B and 10C).

This method of synthesis may also be used to record and change molecular environments. For example, if a surface has several chimeric strands exposed, then each time a primer binds to one of the sites it permanently removes that strand from the surface (FIG. 7A), and this could be visualized at a later time. These primers can record this marking information from their spatial environment by "collecting" the strands from areas that it visits (FIG. 7B). Eventually, a collection can be sequenced to reveal information about the primer's whereabouts over time.

This latter type of collection recording is useful, for example, for studying the spatial orientation of other molecules, such as proteins, that are attached to the primers. If the protein spent most of its time in the vicinity of another protein that had several tethered chimeric strands, then the primer could record this information by collecting the sequence information of those chimeric strands.

Figure 7C:
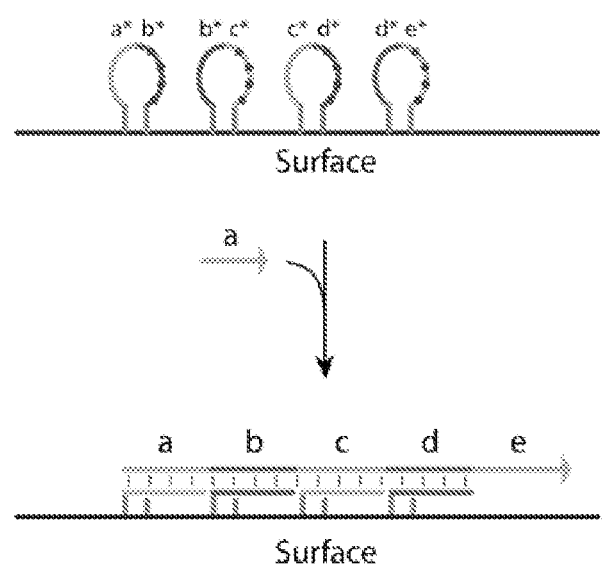

Further, the primer strands may be used as molecular crawlers that irreversibly traverse one chimeric strand at a time. If these surface-bound strands are tethered by two points on a surface, then the primer can permanently bind to them as it records the local molecular landscape (FIG. 7C). As the crawler (primer) moves between sites, it copies the information from the sites and records the information in its growing body (nucleic acid).

Reaction Conditions

Reactions of the present disclosure may proceed as "one-pot synthesis" reactions, whereby a template is subjected to successive and/or simultaneous reactions (e.g., annealing, strand displacement, extension, etc.) in a single vessel. Such reactions may include at least one template strand, at least one primer strand, a polymerase and nucleotide triphosphates. Typically, all the components of a reaction are provided in a reaction buffer, with the exception of RNase, which may be added at a later stage of the reaction (e.g., following polymerization).

In some embodiments, the polymerase is a DNA polymerase (DNAP), such as a DNA polymerase having DNA strand displacing activity (a strand displacement polymerase, or a strand-displacing polymerase). "Strand displacement" describes the ability to displace downstream DNA encountered during synthesis. Examples of polymerases having DNA strand displacement activity that may be used as provided herein include, without limitation, phi29 DNA polymerase (e.g., NEB # M0269), Bst DNA polymerase, large fragment (e.g., NEB # M0275), or Bsu DNA polymerase, large fragment (e.g., NEB # M0330). Other polymerases having strand displacement activity may be used. In some embodiments, the polymerase is a RNA polymerase.

In some embodiments, the polymerase is phi29 DNA polymerase. In such embodiments, the reaction conditions may be as follows: 1X reaction buffer (e.g., 50 mM Tris-HCl, 10 mM $MgCl_2$, 10 mM $(NH_4)_2SO_4$, 4 mM DTT) supplement with purified bovine serum albumin (BSA), pH 7.5, incubated at 30° C.

In some embodiments, the polymerase is Bst DNA polymerase, large fragment. In such embodiments, the reaction conditions may be as follows: 1X reaction buffer (e.g., 20 mM Tris-HCl, 10 mM $(NH_4)_2SO_4$, 10 mM KCl, 2 mM $MgSO_4$, 0.1% TRITON® X-100), pH 8.8, incubated at 65° C.

In some embodiments, the polymerase is Bsu DNA polymerase. In such embodiments, the reaction conditions may be as follows: 1X reaction buffer (e.g., 50 mM NaCl, 10 mM Tris-HCl, 10 mM $MgCl_2$, 1 mM DTT), pH 7.9, incubated at 37° C.

In some embodiments, the polymerase is a non-strand displacing polymerase having reverse transcriptase activity.

The concentration of target sequence, primer(s) and dNTPs in a reaction system may be varied depending, for example, on the particular application (e.g., exponential amplification, real-time monitoring, etc.) and kinetics required for that particular application.

The concentration of primer(s) and/or templates in a reaction may be, for example, 1 nM to 1000 nM. In some embodiments, the nucleic acid concentration in a reaction is 1-10, 1-15, 1-20, 1-30, 1-40, 1-50, 1-60, 1-70, 1-80, 1-90, 1-100, 10-15, 10-20, 10-30, 10-40, 10-50, 10-60, 10-70, 10-80, 10-90, 10-100, 10-125, 10-150, 10-200, 25-50, 25-75, 25-100, 25-150, 25-200, 50-75, 50-100, 50-150 or 50-200 nM. In some embodiments, the nucleic acid concentration in a reaction is 100-200, 100-300, 100-400, 100-500, 100-600, 100-70, 100-800, 100-900 or 100-1000 nM. In some embodiments, the nucleic acid concentration in a reaction is 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195 or 200 nM. In some embodiments, the nucleic acid concentration in a reaction is 100, 200, 300, 400, 500, 600, 700, 800, 900 or 1000 nM. The concentration of nucleic acid in a reaction may be less than 10 nM or greater than 1000 nM.

The concentration of nucleotide triphosphates (e.g., dNTPs or rNTPs) in a reaction may be, for example, 2-1000 µM. In some embodiments, the dNTP or rNTP concentration in a reaction is 2-10 µM, 2-15 µM, 2-20 µM, 2-25 µM, 2-30 µM, 2-35 µM, 2-40 µM, 2-45 µM, 2-50 µM, 2-55 µM, 2-60 µM, 2-65 µM, 2-70 µM, 2-75 µM, 2-80 µM, 2-85 µM, 2-90 µM, 2-95 µM, 2-100 µM, 2-110 µM, 2-120 µM, 2-130 µM, 2-140 µM, 2-150 µM, 2-160 µM, 2-170 µM, 2-180 µM, 2-190 µM, 2-200 µM, 2-250 µM, 2-300 µM, 2-350 µM, 2-400 µM, 2-450 µM, 2-500 µM, 2-600 µM, 2-700 µM, 2-800 µM, 2-900 µM or 2-1000 µM. For example, the dNTP or rNTP concentration in a reaction may be 2 µM, 5 µM, 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µMM, 190 µM, 195 µM, 200 µM, 205 µM, 210 µM, 215 µM, 220 µM, 225 µM, 230 µM, 235 µM, 240 µM, 245 µMM, or 250 µM. In some embodiments, the dNTP or rNTP concentration in a reaction is 10-20 µM, 10-30 µM, 10-40 µM, 10-50 µM, 10-60 µM, 10-70 µM, 10-80 µM, 10-90 µM or 10-100 µM. In some embodiments, the dNTP or rNTP concentration in a reaction is 150-200 µM, 150-225 µM, 150-250 µM, 175-200 µM, 175-225 µM, 175-250 µM, 200-225 µM, 200-250 µM or 200-300 µM.

The kinetics of a reaction may be controlled by varying temperature, time, buffer/salt conditions, and deoxyribonucleotide triphosphate (dNTP) concentrations, for example. Polymerases, like most enzymes, are sensitive to many buffer conditions, including ionic strength, pH and types of metal ions present (e.g., sodium ions vs. magnesium ions). Thus, a temperature at which a polymerase is active (and a reaction is performed) may vary from, for example, 4° C. to 65° C. (e.g., 4° C., 25° C., 37° C., 42° C., 60° C., or 65° C.). In some embodiments, temperature at which a polymerase is active is 4-25° C., 4-30° C., 4-35° C., 4-40° C., 4-45° C., 4-50° C., 4-55° C., 4-60° C., 10-25° C., 10-30° C., 10-35° C., 10-40° C., 10-45° C., 10-50° C., 10-55° C., 10-60° C., 25-30° C., 25-35° C., 25-40° C., 25-45° C., 25-50° C., 25-55° C., 25-60° C., 25-65° C., 35-40° C., 35-45° C., 35-50° C., 35-55° C., 35-60° C., or 35-65° C. In some embodiments, a temperature at which a polymerase is active is at room temperature, while in other embodiments, a reaction is performed at 37° C. In still other embodiments, a reaction is performed at 65° C. In another embodiment, a reaction is performed at 60° C.

The temperature at which a particular double-stranded nucleic acid denatures (dissociates/'melts' into two single strands) may be determined a priori, based, for example, on the length and composition (specific nucleotide sequence) of the template strand. Higher GC content (relative to AT content) requires higher temperatures, for example.

A reaction may be performed (incubated) for 1 minute (min) to an hour (hr), or longer. In some embodiments, an amplification reaction is carried out for 1 min, 2 min, 3 min, 4 min, 5 min, 6 min, 7 min, 8 min, 9 min, 10 min, 15 min, 20 min, 25 min, 30 min, 35 min, 40 min, 45 min, 50 min, 55 min, 60 min, 1 hr, 2 hr, 3 hr, 4 hr, 5 hr, 6 hr, 7 hr, 8 hr, 9 hr, 10 hr, 11 hr, 12 hr, 18 hr or 24 hr. In some embodiments, an amplification reaction is carried out for 2 hr.

In some embodiments, nucleotide triphosphate variants are used. For example, hot start/clean amp dNTPs, phosphorothioate dNTPs, or fluorescent dNTPs. Other nucleotide triphosphate variants may be used.

"Conditions that result in the production of" a particular molecule, for example, "conditions that result in the production of a target amplicon," may be physiological conditions (e.g., a temperature of 20-40 degrees Celsius, atmospheric pressure of 1, and/or a pH value of 6-8). Such reaction conditions may be varied, depending on the nature of the template strand, the primer strand and the temperature at which the enzyme(s) (e.g., polymerase and/or reverse transcriptase) are active.

In some embodiments, a reaction is performed at a temperature of 20 to 40 degrees Celsius (° C.). For example, an amplification reaction may be performed at a temperature of 20° C., 21° C., 22° C., 23° C., 24° C., 25° C., 26° C., 27° C., 28° C., 29° C., 31° C., 32° C., 33° C., 34° C., 35° C., 36° C., 37° C., 38° C., 39° C. or 40° C.

Reaction buffers that may be used for an amplification reaction include, without limitation, "Thermo-Pol Buffer" (New England Biolabs), phosphate buffered saline (with or without Mg or Na supplementation), any commercial or laboratory-prepared cell media, water or any pH-buffered solution supplemented with cationic salts sufficient for DNA hybridization and polymerase operation. Reaction buffer, in some embodiments, may have a salt concentration of 0.25-15 mM Mg and/or 50-250 mM Na.

Methods

Some aspects of the present disclosure provide a method of producing a nucleic acid comprising: combining in reaction buffer that contains a polymerase (a) a template strand comprising (i) a 5' domain that comprises deoxyribonucleotides interspersed with ribonucleotides, and (ii) a 3' domain, and (b) a primer strand comprising a nucleotide domain that is complementary to the 3' domain of the template strand; incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid. See, e.g., FIGS. 1A and 1B.

Some aspects of the present disclosure provide a method of producing a nucleic acid comprising: combining in reaction buffer that contains a polymerase (a) a plurality of template strands, each comprising (i) a 5' domain that comprises deoxyribonucleotides interspersed with ribonucleotides, and (ii) a 3' domain, wherein the 5' domain of each template strand has the same nucleotide composition as the 3' domain of only one other template strand of the plurality, and (b) a primer strand comprising a nucleotide domain that is complementary to the 3' domain of only one of the template strands of the plurality; incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid. See, e.g., FIGS. 1C and 1D.

In some embodiments, a template strand further comprises a 3' stopper.

In some embodiments, a 3' domain of the template strand comprises deoxyribonucleotides interspersed with ribonucleotides. In some embodiments, a 3' domain of the template strand comprises nucleotides that consist of deoxyribonucleotides (all nucleotides of the 3' domain are deoxyribonucleotides).

In some embodiments, a template strand has a length of 20-100 nucleotides. In some embodiments, a 3' domain of the template strand has a length of 10-50 nucleotides. In some embodiments, a 5' domain of the template strand has a length of 10-50 nucleotides.

In some embodiments, at least 50% (e.g., 50%, 55%, 60%, 65%, 70%, 75%, 80%, 85%, 90%, or 95%) of the nucleotides of the template strand are deoxyribonucleotides, and the remaining nucleotides are ribonucleotides. In some embodiments, at least 90% (e.g., 90%, 91%, 92%, 93%, 94%, 95%, 96%, 97%, 98%, 99%) of the nucleotides of the template strand are deoxyribonucleotides, and the remaining nucleotides are ribonucleotides.

In some embodiments, a primer strand has a length of 10-50 nucleotides. In some embodiments, a primer strand comprises deoxyribonucleotides or comprises nucleotides that consist of deoxyribonucleotides.

In some embodiments, a template strand is linked to a detectable molecule. See, e.g., FIGS. 6A and 6B.

In some embodiments, a detectable molecule is a fluorophore. In some embodiments, a template strand is linked to a biomolecule (e.g., a polynucleotide or a polypeptide).

The present disclosure also provide, in some aspects, a method of producing a nucleic acid comprising: combining in reaction buffer that contains a strand-displacing polymerase (a) a first primer strand comprising (i) a 5' domain that comprises deoxyribonucleotides interspersed with ribonucleotides, and (ii) a 3' domain, and (b) a template strand comprising a 3' domain that is complementary to the 3' domain of the first primer strand; incubating the reaction mixture under conditions that result in DNA polymerization to produce a first double-stranded nucleic acid; incubating the first double-stranded nucleic acid in reaction buffer that contains ribonuclease H (RNase H) under conditions that result in enzymatic cleavage of the first double-stranded nucleic acid to produce a first partially double-stranded nucleic acid comprising a toehold domain that is complementary to the 5' domain of the first primer strand; and incubating the partially double-stranded nucleic acid in reaction buffer in the presence of the first primer strand and strand-displacing polymerase under conditions that result in DNA polymerization to produce a second double-stranded nucleic acid, thereby displacing one strand of the first double-stranded nucleic acid. See, e.g., FIG. 2A.

In some embodiments, the method further comprises incubating the displaced strand of the first double-stranded nucleic acid in reaction buffer in the presence of a strand-displacing polymerase and a second primer strand that comprises (i) 5' domain that comprises deoxyribonucleotides interspersed with ribonucleotides and (ii) a 3' domain that is complementary to a 3' domain of the displaced strand, under conditions that result in DNA polymerization to produce a third double-stranded nucleic acid. See, e.g., FIG. 2B (steps 1-3).

In some embodiments, the method further comprises incubating the third double-stranded nucleic acid in reaction buffer that contains RNase H under conditions that result in enzymatic cleavage of the third double-stranded nucleic acid to produce a second partially double-stranded nucleic acid comprising a toehold domain that is complementary to the 5' domain of the second primer strand. See, e.g., FIG. 2B (step 4).

In some embodiments, the method further comprises incubating the second partially double-stranded nucleic acid in reaction buffer in the presence of the second primer strand and strand-displacing polymerase under conditions that result in DNA polymerization to produce a fourth double-stranded nucleic acid, thereby displacing one strand of the third double-stranded nucleic acid. See, e.g., FIG. 2B (steps 5-6).

In some aspects, provide herein is a method of producing a nucleic acid comprising: combining in reaction buffer that contains a strand-displacing polymerase (a) a first template strand comprising (i) a 5' domain that comprises a 5' subdomain and a 3' subdomain and (ii) a 3' domain that comprises a 5' subdomain and a 3' subdomain,(b) a second template strand comprising (i) a 5' domain that comprises a 5' subdomain and a 3' subdomain and (ii) a 3' domain that comprises a 5' subdomain and a 3' subdomain, (c) a first primer strand that comprises (i) a 5' domain that comprises deoxyribonucleotides interspersed with ribonucleotides, and (ii) a 3' domain, wherein the 5' domain of the first primer strand is complementary to the 3' subdomain of the 3' domain of the first template strand, and the 3' domain of the first primer strand is complementary to the 5' subdomain of the 3' domain of the first template strand, and (d) a second primer strand that comprises (i) a 5' domain that comprises deoxyribonucleotides interspersed with ribonucleotides, and (ii) a 3' domain, wherein the 5' domain of the second primer strand is complementary to the 3' subdomain of the 3' domain of the second template strand, and the 3' domain of the second primer strand is complementary to the 5' subdomain of the 3' domain of the second template strand (see, e.g., FIG. 3, steps 1-2); incubating the reaction mixture under conditions that result in DNA polymerization to produce double-stranded nucleic acids (see, e.g., FIG. 3, step 3); and incubating the double-stranded nucleic acids in reaction buffer that contains ribonuclease H (RNase H) under conditions that result in enzymatic cleavage of the double-stranded nucleic acids (see, e.g., FIG. 3, step 4).

Methods of producing a nucleic acid include methods of amplifying a nucleic acid, for example, exponentially amplifying a nucleic acid. Thus, some aspects of the present disclosure provide a method of exponentially amplifying a nucleic acid comprising: combining in reaction buffer that contains a strand-displacing polymerase (a) a first template strand comprising (i) a 5' domain that comprises a 5' subdomain and a 3' subdomain and (ii) a 3' domain that comprises a 5' subdomain and a 3' subdomain,(b) a second template strand comprising (i) a 5' domain that comprises a 5' subdomain and a 3' subdomain and (ii) a 3' domain that comprises a 5' subdomain and a 3' subdomain, (c) a first primer strand that comprises (i) a 5' domain that comprises deoxyribonucleotides interspersed with ribonucleotides, and (ii) a 3' domain, wherein the 5' domain of the first primer strand is complementary to the 3' subdomain of the 3' domain of the first template strand, and the 3' domain of the first primer strand is complementary to the 5' subdomain of the 3' domain of the first template strand, and (d) a second primer strand that comprises (i) a 5' domain that comprises deoxyribonucleotides interspersed with ribonucleotides, and (ii) a 3' domain, wherein the 5' domain of the second primer strand is complementary to the 3' subdomain of the 3' domain of the second template strand, and the 3' domain of the second primer strand is complementary to the 5' subdomain of the 3' domain of the second template strand (see, e.g., FIG. 3, steps 1-2); incubating the reaction mixture under conditions that result in DNA polymerization to produce double-stranded nucleic acids (see, e.g., FIG. 3, step 3); incubating the double-stranded nucleic acids in reaction buffer that contains ribonuclease H (RNase H) under conditions that result in enzymatic cleavage of the double-stranded nucleic acids (see, e.g., FIG. 3, step 4); incubating the cleaved double-stranded nucleic acids in the presence of a strand-displacing polymerase, the first primer and the second primer under conditions that result in polymerization and displacement of one of the strands of the cleaved double-stranded nucleic acids (see, e.g., FIG. 3, steps 5-6); incubating the displaced strands in the presence of a strand-displacing polymerase, the first primer and the second primer under conditions that result in polymerization (see, e.g., FIG. 3, steps 7-8) to produce additional double-stranded nucleic acids; incubating the additional double-stranded nucleic acids in the presence of RNase H under conditions that result in enzymatic cleavage of the double-stranded nucleic acids (see, e.g., FIG. 3, step 9); and incubating the cleaved double-stranded nucleic acids in the presence of a strand-displacing polymerase, the first primer and the second primer under conditions that result in polymerization and displacement of one of the strands of the cleaved double-stranded nucleic acids (see, e.g., FIG. 3, steps 10-11), thereby exponentially amplifying the first and second template strands.

In some aspects, the present disclosure provide a method of producing a nucleic acid comprising: combining in reaction buffer that contains a strand-displacing polymerase (a) a first template strand comprising a 5' domain and a 3' domain, (b) a second template strand comprising a 5' domain and a 3' domain, (c) a first primer strand that comprises (i) a 5' domain that comprises deoxyribonucleotides interspersed with ribonucleotides, and (ii) a 3' domain, wherein the 3' domain of the first primer strand is complementary to the 3' domain of the second template strand, and (d) a second primer strand that comprises (i) a 5' domain that comprises deoxyribonucleotides interspersed with ribonucleotides, and (ii) a 3' domain, wherein the 3' domain of the second primer strand is complementary to the 3' domain of the first template strand (see, e.g., FIG. 4, step 1); incubating the reaction mixture under conditions that result in DNA polymerization to produce double-stranded nucleic acids (see, e.g., FIG. 4, step 2); and incubating the double-stranded nucleic acids in reaction buffer that contains ribonuclease H (RNase H) under conditions that result in enzymatic cleavage of the double-stranded nucleic acids (see, e.g., FIG. 4, step 3).

Also provided herein is a proofreading method to, for example, produce a single-stranded nucleic acid, the method comprising: combining in reaction buffer that contains non-strand-displacing polymerase with reverse transcriptase activity a) a template strand comprising in the 5' to 3' orientation a first domain, a second domain, a third domain, and a fourth domain, wherein the first domain and the third domain are complementary to and bound to each other, and wherein a stopper is located between the first domain and the second domain, and (b) a primer strand comprising in the 5' to 3' orientation a first domain and a second domain, wherein the first domain of the primer strand is complementary fourth domain of the template strand, and wherein the second domain of the primer strand is complementary to the third domain of the template strand; and incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid. See, e.g., FIGS. 5A and 5B.

Further provided herein is a method of molecular landscape probing comprising: combining in reaction buffer that contains polymerase (a) a substrate (e.g., a glass or silicone substrate) comprising a plurality of nucleic acids, wherein each nucleic acid comprises (i) a 5' domain that comprises deoxyribonucleotides interspersed with ribonucleotides, and (ii) a 3' domain, and wherein each nucleic acid is attached to the substrate through its 5' domain, and (b) a primer strand that is complementary to at least one 3' domain of a nucleic acid of the plurality; incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid. See, e.g., FIGS. 7A-7C.

In some embodiments, the 5' domain of each nucleic acid of the plurality strand has the same nucleotide composition as the 3' domain of at most one other template strand of the plurality. In some embodiments, each nucleic acid is attached to the substrate through both its 5' domain and its 5' domain.

Some aspects of the present disclosure provide a method of producing a nucleic acid comprising: combining in reaction buffer that contains strand-displacing polymerase (a) a template strand comprising at least one ribonucleotide adjacent to a stopper separating a 5' domain from a 3' domain, and (b) a primer strand comprising a domain that is complementary to the 3' domain of the template strand; incubating the reaction mixture under conditions that result in DNA polymerization to produce a double-stranded nucleic acid; and incubating the double-stranded nucleic acid in reaction buffer that contains ribonuclease H (RNase H) under conditions that result in enzymatic cleavage of the double-stranded nucleic acid. See, e.g., FIGS. 10A-10C.

In some embodiments, the stopper is upstream from the at least one ribonucleotide. In some embodiments, the stopper is a C3 spacer phosphoramidite, a short triethylene glycol spacer, a 1',2'-dideoxyribose, or a sequence of at least one 2'-O-methyl ribonucleotides.

Compositions and Kits

Also provided herein is a composition or kit comprising: (a) a first template strand comprising a 5' domain and a 3' domain; (b) a second template strand comprising a 5' domain and a 3' domain, wherein the 5' domain of the first template strand is complementary to the 3' domain of the second template strand, and wherein the 3' domain of the first template strand is complementary to the 5' domain of the second template strand; (c) a first primer strand comprising (i) a 5' domain that comprises deoxyribonucleotides interspersed with ribonucleotides, and (ii) a 3' domain that is complementary to the 3' domain of the first template strand; and (d) a first primer strand comprising (i) a 5' domain that comprises deoxyribonucleotides interspersed with ribonucleotides, and (ii) a 3' domain that is complementary to the 3' domain of the second template strand. In some embodiments, the composition further comprises a strand-displacing polymerase. In some embodiments, the composition further comprises RNase H.

Further provided herein is a composition or kit comprising: (a) a template strand comprising in the 5' to 3' orientation a first domain, a second domain, a third domain, and a fourth domain, wherein the first domain and the third domain are complementary to and bound to each other, and wherein a stopper is located between the first domain and the second domain; and (b) a primer strand comprising in the 5' to 3' orientation a first domain and a second domain, wherein the first domain of the primer strand is complementary fourth domain of the template strand, and wherein the second domain of the primer strand is complementary to the third domain of the template strand. In some embodiments, the composition further comprises a non-strand displacing polymerase with reverse transcriptase activity. In some embodiments, the composition further comprises RNase H.

Further still, provided herein is a composition or kit comprising: (a) a substrate comprising a plurality of nucleic acids, wherein each nucleic acid comprises (i) a 5' domain that comprises deoxyribonucleotides interspersed with ribonucleotides, and (ii) a 3' domain, and wherein each nucleic acid is attached to the substrate through its 5' domain, and (b) a primer strand that is complementary to at least one 3' domain of a nucleic acid of the plurality. In some embodiments, the composition further comprises a polymerase. In some embodiments, the composition further comprises RNase H.

Some aspects of the present disclosure provide a composition or kit comprising (a) a template strand comprising at least one ribonucleotide adjacent to a stopper separating a 5' domain from a 3' domain, and (b) a primer strand comprising a domain that is complementary to the 3' domain of the template strand. In some embodiments, the composition further comprises a polymerase. In some embodiments, the composition further comprises RNase H.

EXAMPLES

Example 1: Amplification of Target Sequences

Figure 8:
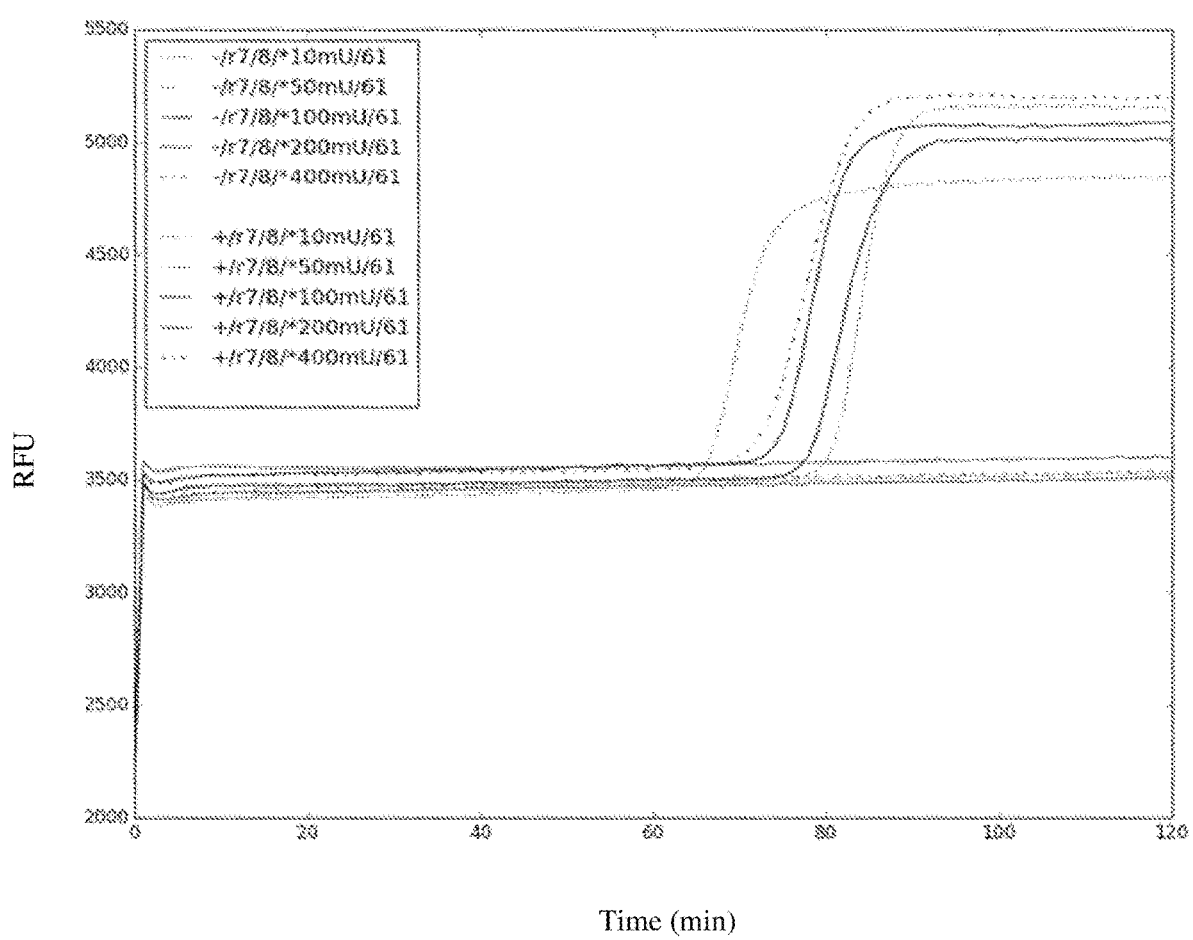
FIG. 8 shows real-time amplification curves of samples with or without target sequences under different enzyme ratios. The target concentration was 0.85 fM and the amplification primers tested contained seven RNA bases.
Figure 9:
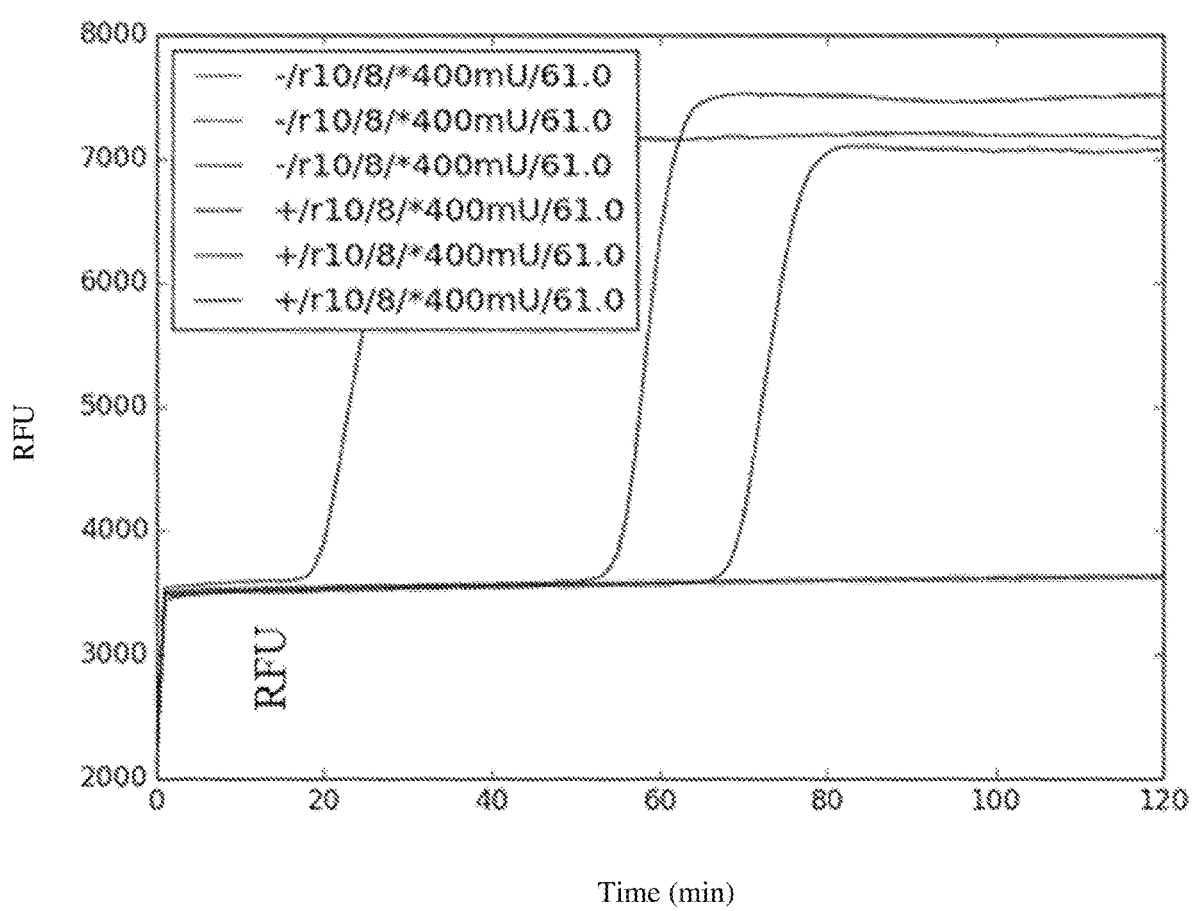
FIG. 9 shows real-time amplification curves of samples with or without target sequences under different enzyme ratios. The target concentration was 0.85 fM and the amplification primers tested contained seven RNA bases.

The amplification of nucleotide samples using the method of the present disclosure was tested. Real-time amplification curves of samples with or without target sequences under different enzyme ratios are provided in FIGS. 8 and 9. The target concentration was 0.85 fM and the amplification primers tested contained seven RNA bases.

Example 2: Validation of RNase H-coupled Synthesis

Figure 11A:
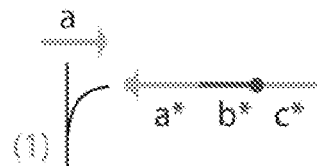
FIGS. 11A-11D show an experimental validation of RNase H-coupled synthesis.
Figure 11A:
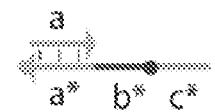
Figure 11A:
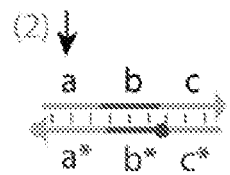
Figure 11A:
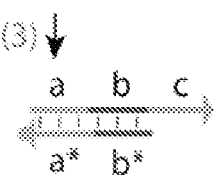

Experiments were performed to validate the one-step reactions described herein. The basic one-step reaction scheme, to append the domains b and c onto a primer ending in domain a using a chimeric template strands (c*b*a*), is shown schematically in FIG. 11A. Essentially, the primer (a) binds to the template (c*b*a*) and extends on the template, creating a double-stranded nucleic acid strand. Then, RNase H2 (or a similar enzyme) cleaves the RNA base (or bases) to expose a primer overhang which can then be used for the next step of the cascade.

Figure 11B:
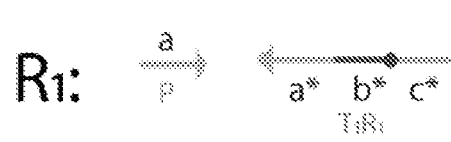
Figure 11B:
Figure 11B:
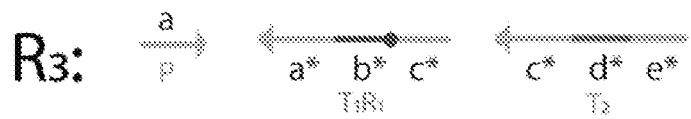
Figure 11B:
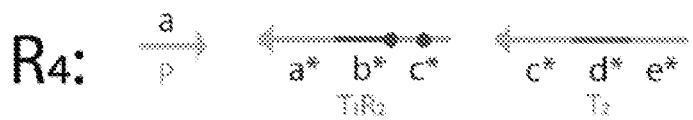

In the experiments, four different reaction conditions were tested, as illustrated in FIG. 11B. Templates were constructed with one ($T_1R_1$) or two ($T_1R_2$) RNA bases interspersed (intercalated) with the DNA bases. The sequences of each are given below. Then, four different reaction component set conditions were tested: $R_1$, testing a primer combined with a template containing a single RNA base; $R_2$, testing a primer combined with a template containing two RNA bases; $R_3$, testing $R_1$ conditions but with an additional extension template ($T_2$) used to validate cascading; and $R_4$, testing $R_2$ but also with the additional template ($T_2$). Reactions were run for 2 hours at 60° C. followed by 20 minutes of heat inactivation at 80° C. in 1x isothermal amplification buffer using 800 units/ml Bst LF polymerase, 20 mU per microliter of RNase H2, 10 nM primer, 20 nM templates, and 200 µM dNTPs.

Figure 11C:
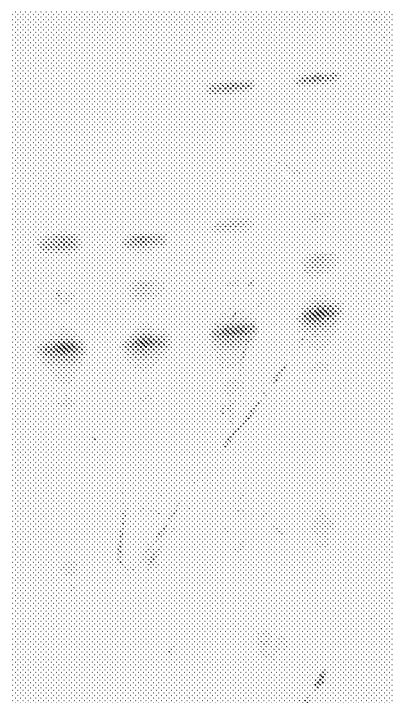

The reactions were run on a 15% PAGE TBE-urea denaturing gel at 200V for 35 minutes to visualize the extension lengths of the FAM-labeled primer, and band lengths were labeled with their presumed sequence domains. As shown in FIG. 11C, reaction conditions $R_1$ and $R_2$ show a band at the expected length of the a b c product, along with some leftover a b product due to premature cleavage by RNase H2. Reactions $R_3$ and $R_4$ show a band at the expected length of the a b c d e product, indicating successful cascading of the synthesis reactions.

Figure 11D:
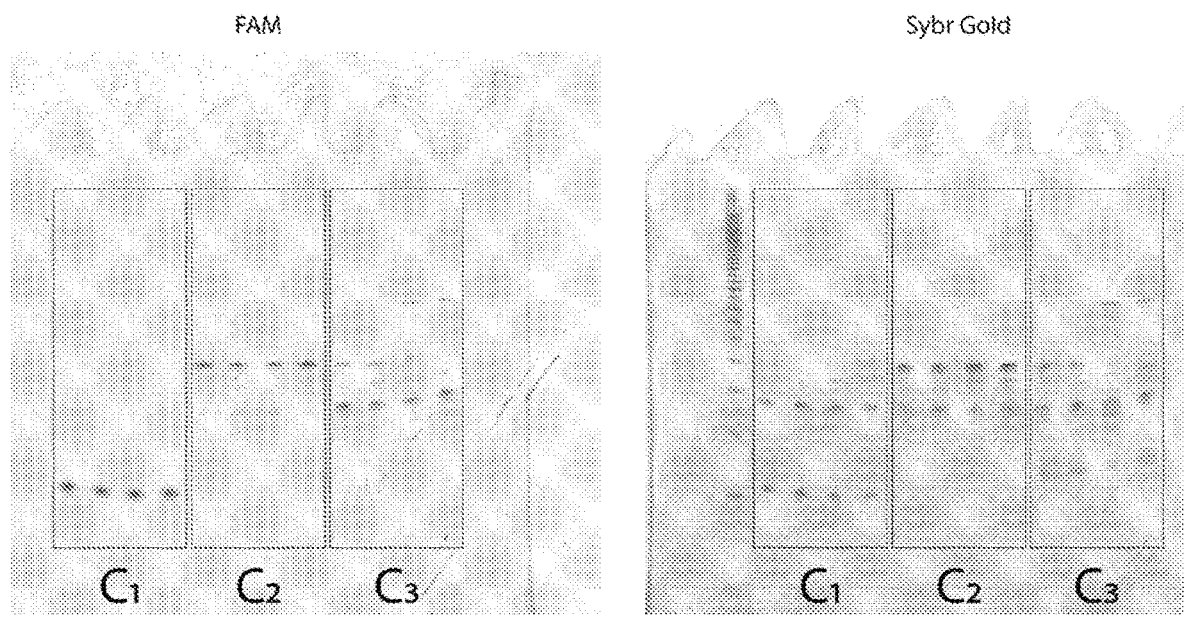

The templates from reactions $R_1$ to $R_4$ (left to right in FIG. 11D) were subjected to additional control conditions, as follows: $C_1$ with no enzymes, $C_2$ with just the polymerase, and $C_3$ with both the polymerase and RNase H2 enzyme. As shown in FIG. 11D, the cascading behavior was only shown in the presence of both enzymes (condition $C_3$). Without the RNase H2 (condition $C_2$), the primer domain c is not exposed and cannot cascade into the next synthesis step.

Sequences Used in Example 2

Primer:
(SEQ ID NO: 1)
/56-FAM/ATATGACTCCAC TCACGGCC

T₁R₁:
(SEQ ID NO: 2)
TCTTTCACTTCAA rC GGTACCGTCGAAAC GGCCGTGA TT

T₁R₂:
(SEQ ID NO: 3)
TCTTTC rA CTTCAA rC GGTACCGTCGAAAC GGCCGTGA TT

T₂:
(SEQ ID NO: 4)
GATTTTTTTACCGT TAACGATCAGATGACCG TCTTTCACTTCAA TT

All sequences have TT at the end to prevent their extension. Bases with a lower case "r" in front of them correspond to RNA bases.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of producing a nucleic acid comprising:
combining in reaction buffer that contains a polymerase
(a) a template strand comprising (i) a 5' domain that comprises deoxyribonucleotides interspersed with ribonucleotides, and (ii) a 3' domain, and
(b) a primer strand comprising a nucleotide domain that is complementary to the 3' domain of the template strand;
incubating the reaction mixture under conditions that result in DNA polymerization to produce a double-stranded nucleic acid; and
incubating the double-stranded nucleic acid in reaction buffer that contains ribonuclease H (RNase H) under conditions that result in enzymatic cleavage of the double-stranded nucleic acid.

2. The method of claim 1, wherein the template strand further comprises a 3' stopper and/or a stopper located between the 5' domain and the 3' domain.

3. The method of claim 1, wherein the 3' domain of the template strand comprises deoxyribonucleotides interspersed with ribonucleotides.

4. The method of claim 1, wherein the 3' domain of the template strand comprises nucleotides that consist of deoxyribonucleotides.

5. The method of any one of claims 1, wherein the template strand has a length of 20-100 nucleotides, the 3' domain of the template strand has a length of 10-50 nucleotides, the 5' domain of the template strand has a length of 10-50 nucleotides, and/or the primer strand has a length of 10-50 nucleotides.

6. The method of claims 1, wherein at least 50% of the nucleotides of the template strand are deoxyribonucleotides, and the remaining nucleotides are ribonucleotides.

7. The method of claims 1, wherein at least 90% of the nucleotides of the template strand are deoxyribonucleotides, and the remaining nucleotides are ribonucleotides.

8. The method of claims 1, wherein the template strand is linked to a detectable molecule.

9. The method of claims 1, wherein the template strand is linked to a biomolecule.

10. The method of claim 1 comprising a plurality of template strands, wherein the 5' domain of each template strand has the same nucleotide composition as the 3' domain of only one other template strand of the plurality, and wherein the
primer strand comprises a nucleotide domain that is complementary to the 3' domain of only one of the template strands of the plurality.

11. The method of claim 1, wherein the polymerase is a non-strand-displacing polymerase with reverse transcriptase activity, wherein
the 5' domain of the template strand comprises a first domain and a second domain, the 3' domain of the template strand comprises a third domain and a fourth domain, wherein the first domain and the third domain are complementary to and bound to each other, and wherein a stopper is located between the first domain and the second domain, and the
primer strand comprises a first domain and a second domain, wherein the first domain of the primer strand is complementary to the fourth domain of the template strand, and wherein the second domain of the primer strand is complementary to the third domain of the template strand.

12. The method of claim 2, wherein the stopper is a C3 spacer phosphoramidite, a short triethylene glycol spacer, a 1',2'-Dideoxyribose, or a sequence of at least one 2'-O-methyl ribonucleotides.

* * * * *

UNITED STATES PATENT AND TRADEMARK OFFICE
CERTIFICATE OF CORRECTION

PATENT NO. : 11,193,153 B2
APPLICATION NO. : 16/495721
DATED : December 7, 2021
INVENTOR(S) : Feng Xuan et al.

It is certified that error appears in the above-identified patent and that said Letters Patent is hereby corrected as shown below:

In the Claims

Claim 5 at Column 25, Line 43 should read:
The method of claim 1, wherein the

Claim 6 at Column 25, Line 49 should read:
The method of claim 1, wherein at least 50% of the Claim 7 at Column 26, Line 16 should read:
The method of claim 1, wherein at least 90% of the Claim 8 at Column 26, Line 19 should read:
The method of claim 1, wherein the template strand is Claim 9 at Column 26, Line 21 should read:
The method of claim 1, wherein the template strand is Signed and Sealed this
Seventeenth Day of May, 2022

Katherine Kelly Vidal
*Director of the United States Patent and Trademark Office*

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: modified by /56-FAM/

<400> SEQUENCE: 1
atatgactcc actcacggcc                                              20

<210> SEQ ID NO 2
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (14)..(14)
<223> OTHER INFORMATION: corresponds to an RNA base

<400> SEQUENCE: 2
tctttcactt caacggtacc gtcgaaacgg ccgtgatt                          38

<210> SEQ ID NO 3
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(7)
<223> OTHER INFORMATION: corresponds to an RNA base
<220> FEATURE:
<221> NAME/KEY: misc_feature
<222> LOCATION: (14)..(14)
<223> OTHER INFORMATION: corresponds to an RNA base

<400> SEQUENCE: 3
```

```
tctttcactt caacggtacc gtcgaaacgg ccgtgatt                                    38
```

<210> SEQ ID NO 4
<211> LENGTH: 46
<212> TYPE: DNA
<213> ORGANISM: Artificial Sequence
<220> FEATURE:
<223> OTHER INFORMATION: Synthetic polynucleotide

<400> SEQUENCE: 4

```
gatttttta ccgttaacga tcagatgacc gtctttcact tcaatt                            46
```